(12) United States Patent
Thompson

(10) Patent No.: US 8,575,923 B1
(45) Date of Patent: Nov. 5, 2013

(54) METHOD AND APPARATUS FOR SPECIAL END AREA INSPECTION

(75) Inventor: Carroll Roy Thompson, Spring, TX (US)

(73) Assignee: OilPatch Technology, Houston, TX (US)

( * ) Notice: Subject to any disclaimer, the term of this patent is extended or adjusted under 35 U.S.C. 154(b) by 181 days.

(21) Appl. No.: 13/374,712

(22) Filed: Jan. 9, 2012

Related U.S. Application Data

(60) Provisional application No. 61/460,785, filed on Jan. 7, 2011.

(51) Int. Cl.
*G01R 33/12* (2006.01)
*G01N 27/72* (2006.01)
*G01N 27/82* (2006.01)
*G01N 27/84* (2006.01)

(52) U.S. Cl.
USPC ........... 324/240; 324/216; 324/232; 324/239; 324/243

(58) Field of Classification Search
USPC ........................................................ 324/240
See application file for complete search history.

(56) References Cited

U.S. PATENT DOCUMENTS

| | | | |
|---|---|---|---|
| 3,073,212 A | 1/1963 | Dunsheath et al. |
| 3,480,855 A | 11/1969 | Lorenzi |
| 3,609,532 A | 9/1971 | Van Kirk |
| 3,614,604 A | 10/1971 | Reinshagen |
| 3,668,517 A | 6/1972 | Zemberry |
| 3,710,236 A | 1/1973 | Halsey et al. |
| 3,774,030 A | 11/1973 | O'Connor et al. |
| 3,872,378 A | 3/1975 | Shiraiwa et al. |
| 4,341,997 A | 7/1982 | Borrows |
| 4,439,730 A | 3/1984 | Kauffman |
| 4,477,776 A | 10/1984 | Spierer |
| 4,482,865 A | 11/1984 | George, Jr. |
| 4,510,447 A | 4/1985 | Moyer |
| 4,675,604 A | 6/1987 | Moyer et al. |
| 4,694,247 A | 9/1987 | Meili et al. |
| 4,792,755 A | 12/1988 | Huschelrath et al. |
| 5,534,775 A | 7/1996 | Lam et al. |
| 6,246,235 B1 | 6/2001 | Lowden et al. |
| 6,683,641 B1 | 1/2004 | MacCracken et al. |
| 6,820,653 B1 | 11/2004 | Schempf et al. |
| 6,904,818 B2 | 6/2005 | Harthorn et al. |

FOREIGN PATENT DOCUMENTS

| | | |
|---|---|---|
| DE | 3337893 A1 | 5/1985 |
| EP | 0442267 B1 | 1/1991 |
| FR | 2946752 A1 | 6/2010 |
| WO | WO 96/31767 A1 | 10/1996 |
| WO | WO 2009/123847 A1 | 10/2009 |

*Primary Examiner* — Bot Ledynh
(74) *Attorney, Agent, or Firm* — Bracewell & Giuliani LLP

(57) ABSTRACT

A magnetic inspection station for tubular members and methods for operating the same have a longitudinal flaw detection assembly adapted to pass a circumferential magnetic field through a tubular member and a transverse flaw detection assembly adapted to pass a longitudinal magnetic field through the tubular member. The magnetic fields cause congregation of a ferromagnetic particles sprayed on the tubular member in a magnetic particle inspection fluid. The congregation of ferromagnetic particles indicates a flaw in the tubular member. The magnetic inspection station includes a clamping apparatus positioned closely adjacent to the magnetic inspection station and adapted to support the tubular member within the magnetic inspection station and exert a compensating force on the tubular member to resist the magnetic forces generated by the longitudinal flaw detection assembly and the transverse flaw detection assembly.

20 Claims, 13 Drawing Sheets

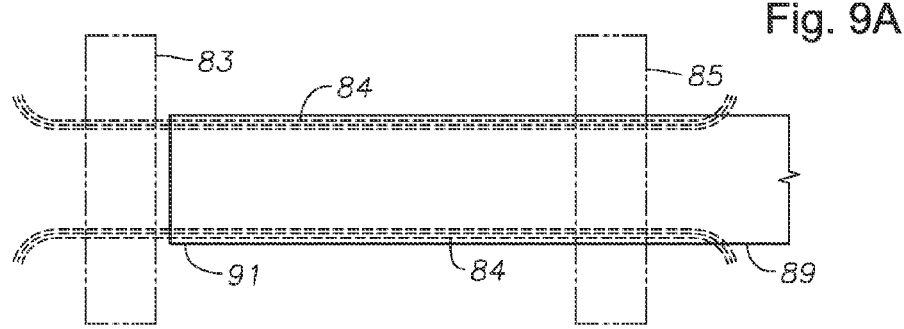
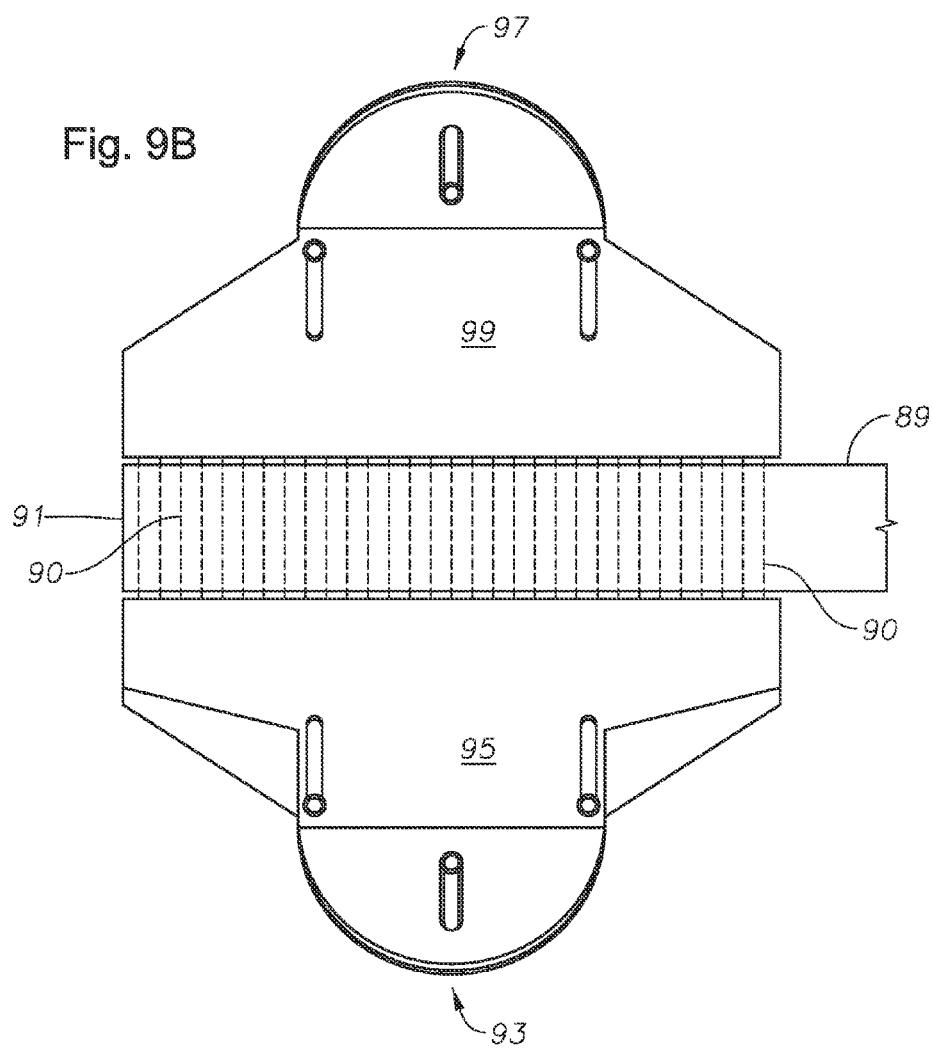

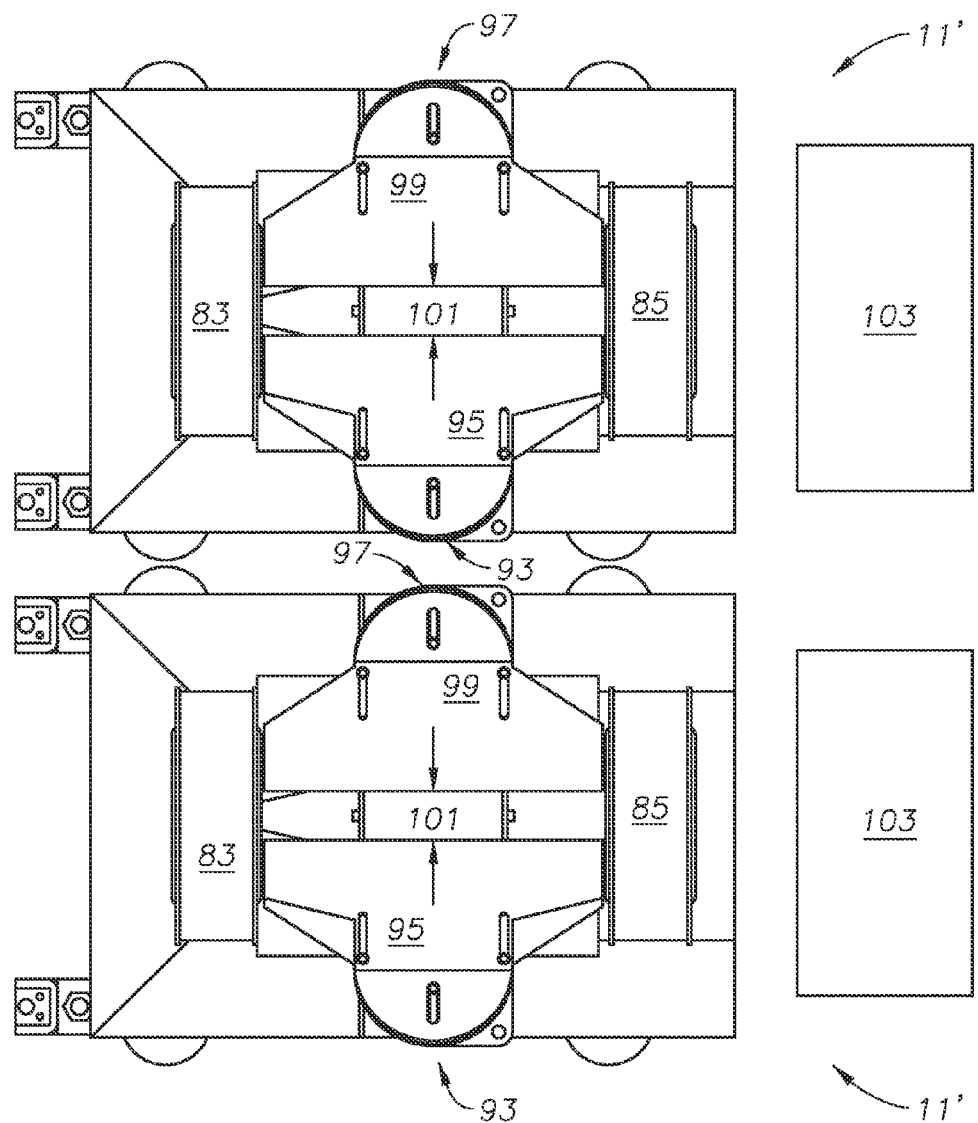

METHOD AND APPARATUS FOR SPECIAL END AREA INSPECTION

This application claims priority to and the benefit of U.S. Provisional Application No. 61/460,785, filed on Jan. 7, 2011, entitled "Method and Apparatus for Special End Area Inspection" to Carroll Roy Thompson which application is hereby incorporated in its entirety herein by reference.

BACKGROUND OF THE INVENTION

1. Field of the Invention

The present invention relates in general to a method and apparatus for inspecting tubular members and, in particular, to an apparatus and method for inspecting tubular couplers and tubular member ends.

2. Brief Description of Related Art

Tubular members are often inspected by passing magnetic fields through the tubular member. Where a flaw is found in a wall of the tubular member, the magnetic field will deviate causing magnetic flux to leak from the surface of the tubular member. A suspension containing ferromagnetic particles visible to the human eye under appropriate conditions is sprayed on the tubular member while the tubular member rotates within the magnetic field. Deviation of the magnetic field and flux leakage cause a congregation of ferromagnetic particles disposed on the surface of the tubular member at the site of the deviation of the magnetic field. The location of the congregation may be marked to identify the flaw in the tubular member. This process may cause an undesirable residual magnetization of the tubular member.

When inspecting the end areas of tubular members or short coupler tubular members, the short length of the end or coupler may cause deviation of the magnetic field and end flux leakage that is unrelated to a flaw in the end or coupler. These deviations and end flux leakage will appear as tubular member flaws. Thus, a special apparatus is needed to closely control the passage of the magnetic field through the tubular member when inspecting the ends of a tubular member or a tubular coupler. These special apparatuses are adapted to inspect only the ends of a tubular member and are positioned in a manner that may cause the end portion of the tubular member to be pulled into contact with the apparatus when the magnetic field is passed through the tubular member. Therefore, there is a need for an inspection apparatus that inspects tubular member ends and couplers without leaving the tubular member magnetized and does not face the risk of damage caused by contact between the tubular member and the apparatus.

SUMMARY OF THE INVENTION

These and other problems are generally solved or circumvented, and technical advantages are generally achieved, by preferred embodiments of the present invention that provide an apparatus for ends area inspection of a tubular member, inspection of tubular couplers, and methods for inspecting the same.

In accordance with an embodiment of the present invention, a magnetic inspection system to inspect test tubular member ends and couplers is disclosed. The magnetic inspection system includes a longitudinal flaw detection assembly (LFDA) that generates a magnetic field that passes circumferentially through the end of the tubular member, and a transverse flaw detection assembly (TFDA) that generates a magnetic field that passes longitudinally through the end of the tubular member. The magnetic inspection system also includes an inspection station frame assembly positioned on a substantially planar horizontal surface. The LFDA and the TFDA are mounted to the inspection station frame assembly so that the LFDA and the TFDA are spaced-apart from the substantially planar horizontal surface. The LFDA and the TFDA are positioned on the inspection station frame assembly so that the end of the tubular member is positioned in both the LFDA and the TFDA. The magnetic inspection system also includes a magnetic particle inspection (MPI) insertion apparatus adapted to coat the tubular member in an MPI fluid. The MPI fluid has a plurality of ferromagnetic particles suspended therein, the ferromagnetic particles appearing fluorescent when exposed to an ultraviolet light. The magnetic inspection system further includes an ultraviolet light assembly that is adapted to expose an exterior surface of the tubular member to ultraviolet light and an interior surface of the tubular member to ultraviolet light. The magnetic inspection system includes a tubular member clamping apparatus positioned closely adjacent to and separate from the inspection station frame assembly. The tubular member clamping apparatus is adapted to support the tubular member within the LFDA and the TFDA, rotate the tubular member within the LFDA and the TFDA about an axis of the tubular member. The axis is substantially parallel to the substantially planar horizontal surface. The tubular member clamping apparatus exerts a compensating force on the tubular member that resists the magnetic forces of the LFDA exerted on the tubular member during inspection of the tubular member.

In accordance with another embodiment of the present invention, a magnetic inspection system to insect test tubular member ends and couplers is disclosed. The magnetic inspection system includes a longitudinal flaw detection assembly LFDA that generates a magnetic field that passes circumferentially through the end of the tubular member, and a transverse flaw detection assembly (TFDA) that generates a magnetic field that passes longitudinally through the end of the tubular member. The magnetic inspection system also includes an inspection station frame assembly positioned on a substantially planar horizontal surface. The LFDA and the TFDA are mounted to the inspection station frame assembly so that the LFDA and the TFDA are spaced-apart from the substantially planar horizontal surface. The LFDA and the TFDA are positioned on the inspection station frame assembly so that the end of the tubular member is positioned in both the LFDA and the TFDA. The magnetic inspection system also includes a magnetic particle inspection (MPI) insertion apparatus adapted to coat the tubular member in an MPI fluid. The MPI fluid has a plurality of ferromagnetic particles suspended therein the ferromagnetic particles appearing fluorescent when exposed to an ultraviolet light. The magnetic inspection system further includes an ultraviolet light assembly that is adapted to expose an exterior surface of the tubular member to ultraviolet light and an interior surface of the tubular member to ultraviolet light. The magnetic inspection system includes a tubular member clamping apparatus positioned closely adjacent to and separate from the inspection station frame assembly. The tubular member clamping apparatus is adapted to support the tubular member within the LFDA and the TFDA, rotate the tubular member within the LFDA and the TFDA about an axis of the tubular member. The axis is substantially parallel to the substantially planar horizontal surface. The tubular member clamping apparatus exerts a compensating force on the tubular member that resists the magnetic forces of the LFDA exerted on the tubular member during inspection of the tubular member. The tubular member clamping apparatus includes a vertical support beam mounted to the substantially horizontal surface, and a first and second compensating piston assembly each having lower ends mounted to opposite sides of the vertical support beam. Pivotable rollers mount on ends of the respective compensating piston assemblies opposite the vertical support beam. The pivotable rollers support the tubular member. A clamping piston assembly is coupled to a motorized roller to clamp the tubular member between the pivotable rollers and the clamping piston while rotating the tubular member. When the LFDA exerts a magnetic force on the tubular member pulling the tubular member toward a pole of the LFDA, the compensating pistons exert reactive forces on the tubular member to push one or more of the pivotable rollers into tighter contact with the tubular member.

In accordance with yet another embodiment of the present invention, a method for inspecting tubular members is disclosed. The method inserts a tubular member into a longitudinal flaw detection apparatus (LFDA) and a transverse flaw detection apparatus (TFDA). The tubular member is supported by a clamping apparatus adapted to rotate the tubular member on an axis of the tubular member. The method rotates the tubular member with a motorized roller of the clamping apparatus, and passes a magnetic field generated by the LFDA circumferentially through the tubular member while spraying the interior and exterior of the tubular member with a magnetic particle inspection (MPI) fluid having a plurality of ferromagnetic particles that appear fluorescent when exposed to ultraviolet light. The method exposes the interior and exterior of the tubular member to ultraviolet light and identifies areas of congregated MPI in response to the circumferential passage of the magnetic field. The method also passes a magnetic field generated by the TFDA longitudinally through the tubular member while spraying the interior and exterior of the tubular member with the MPI fluid. The method exposes the interior and exterior of the tubular member to ultraviolet light and identifying areas of congregated MPI in response to the longitudinal passage of the magnetic field. In response to generation of magnetic forces by the magnetic fields, the method exerts a counteracting force on the tubular member with the clamping apparatus to prevent contact between the tubular member and the LFDA and the TFDA.

An advantage of the disclosed embodiments is that they provide a magnetic inspection assembly that may inspect the ends of a tubular member or a tubular coupler. In addition, the disclosed embodiments provide an inspection apparatus that does not leave the tubular member or coupler magnetized following the inspection process. Still further, the disclosed embodiments provide an apparatus that prevents contact between the tubular member and the inspection apparatus during the inspection process, thereby preventing damage to the ends area and the inspection apparatus during the inspection process.

BRIEF DESCRIPTION OF THE DRAWINGS

So that the manner in which the features, advantages and objects of the invention, as well as others which will become apparent, are attained and can be understood in more detail, more particular description of the invention may be had by reference to the embodiments thereof which are illustrated in the appended drawings that form a part of this specification. It is to be noted, however, that the drawings illustrate only a preferred embodiment of the invention and are therefore not to be considered limiting of its scope as the invention may admit to other equally effective embodiments.

FIGS. 9A and 9B are schematic representations of magnetic flux lines passing through an end of a tubular member.

FIG. 16 is a top plan view of two inspection stations positioned adjacent to each other for simultaneous inspection of two pipe ends, each having a clamping apparatus.

DETAILED DESCRIPTION OF THE PREFERRED EMBODIMENT

The present invention will now be described more fully hereinafter with reference to the accompanying drawings which illustrate embodiments of the invention. This invention may, however, be embodied in many different forms and should not be construed as limited to the illustrated embodiments set forth herein. Rather, these embodiments are provided so that this disclosure will be thorough, complete, and will fully convey the scope of the invention to those skilled in the art. Like numbers refer to like elements throughout, and the prime notation, if used, indicates similar elements in alternative embodiments.

In the following discussion, numerous specific details are set forth to provide a thorough understanding of the present invention. However, it will be obvious to those skilled in the art that the present invention may be practiced without such specific details. Additionally, for the most part, details concerning power controls, station structural framework, and the like have been omitted inasmuch as such details are not considered necessary to obtain a complete understanding of the present invention, and are considered to be within the skills of persons skilled in the relevant art.

Figure 1:
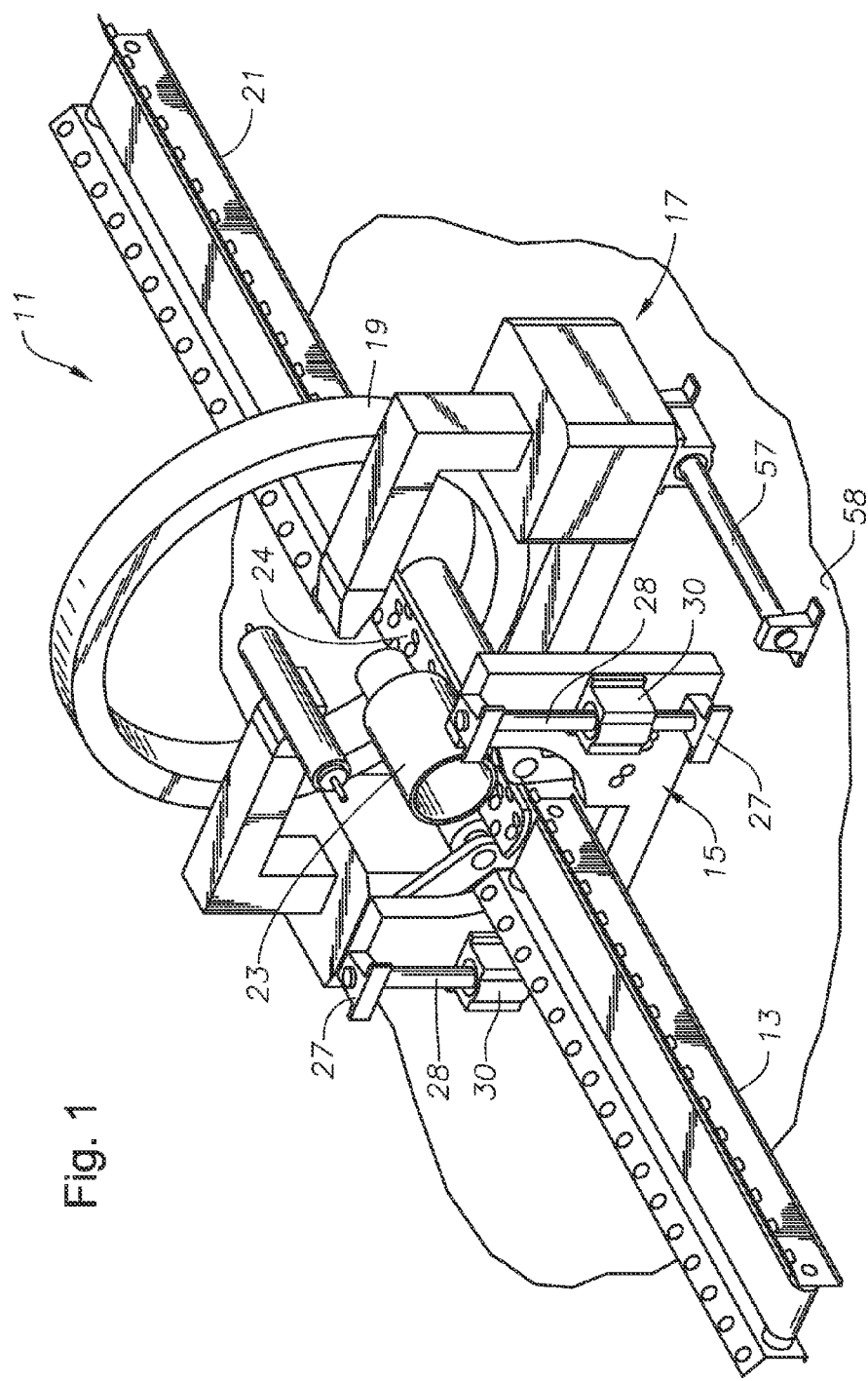
FIG. 1 is schematic perspective view of an exemplary embodiment of an inspection station for inspecting couplers and pipe ends having a coupler in a lower position.

FIG. 1 illustrates an exemplary embodiment of an inspection station 11 for inspecting pipe couplers and pipe ends and detecting anomalies. Inspection station 11 includes a first conveyor 13, a lifting apparatus 15, a longitudinal flaw detection apparatus (LFDA) 17, a transverse flaw detection apparatus (TFDA) 19, and a second conveyor 21. Inspection station 11 of FIG. 1 also includes structural and control components necessary to orient and operate the illustrated components as depicted (not shown). Any number of suitable alternatives exist to provide suitable support and operational control of the inventive components described below. A person skilled in the art will understand that all structural components necessary to position and operate the illustrated components are contemplated and included by the described embodiments.

First and second conveyor 13, 21 each include conveyor belts configured to bring a coupler 23, or a pipe end (not shown), proximate to lifting apparatus 15 prior to inspection and away from lifting apparatus 15 following inspection. Coupler 23 may be a tubular or annular member for coupling or joining to separate tubular members. As shown, first and second conveyors 13, 21 are aligned substantially axially with lifting apparatus 15. Lifting apparatus 15 is configured to receive coupler 23 from conveyor 13 and lift coupler 23 into an appropriate position for inspection of coupler 23, i.e. positioned within one or more magnetic fields as described in more detail below. Lifting apparatus 15 is further configured to lower coupler 23 following inspection for removal of coupler 23 from inspection station 11 by conveyor 21. LFDA 17 is configured to pass a circumferential magnetic field through coupler 23 to inspect coupler 23 for longitudinal flaws in coupler 23. Longitudinal flaws include anomalies in the inspected tubular member that run lengthwise within the tubular member. TFDA 19 is configured to pass a longitudinal magnetic field through coupler 23 to inspect coupler 23 for transverse flaws. Transverse flaws refer to anomalies in the inspected tubular member that run circumferentially within the tubular member. Both longitudinal flaws and transverse flaws may include inclusions, seams, plugs, and the like, and can range in size from barely detectable to the naked eye to up to 2-3 inches in length. Generally, longitudinal and transverse flaws will appear as tight cracks having a width that is barely perceptible.

Figure 2:
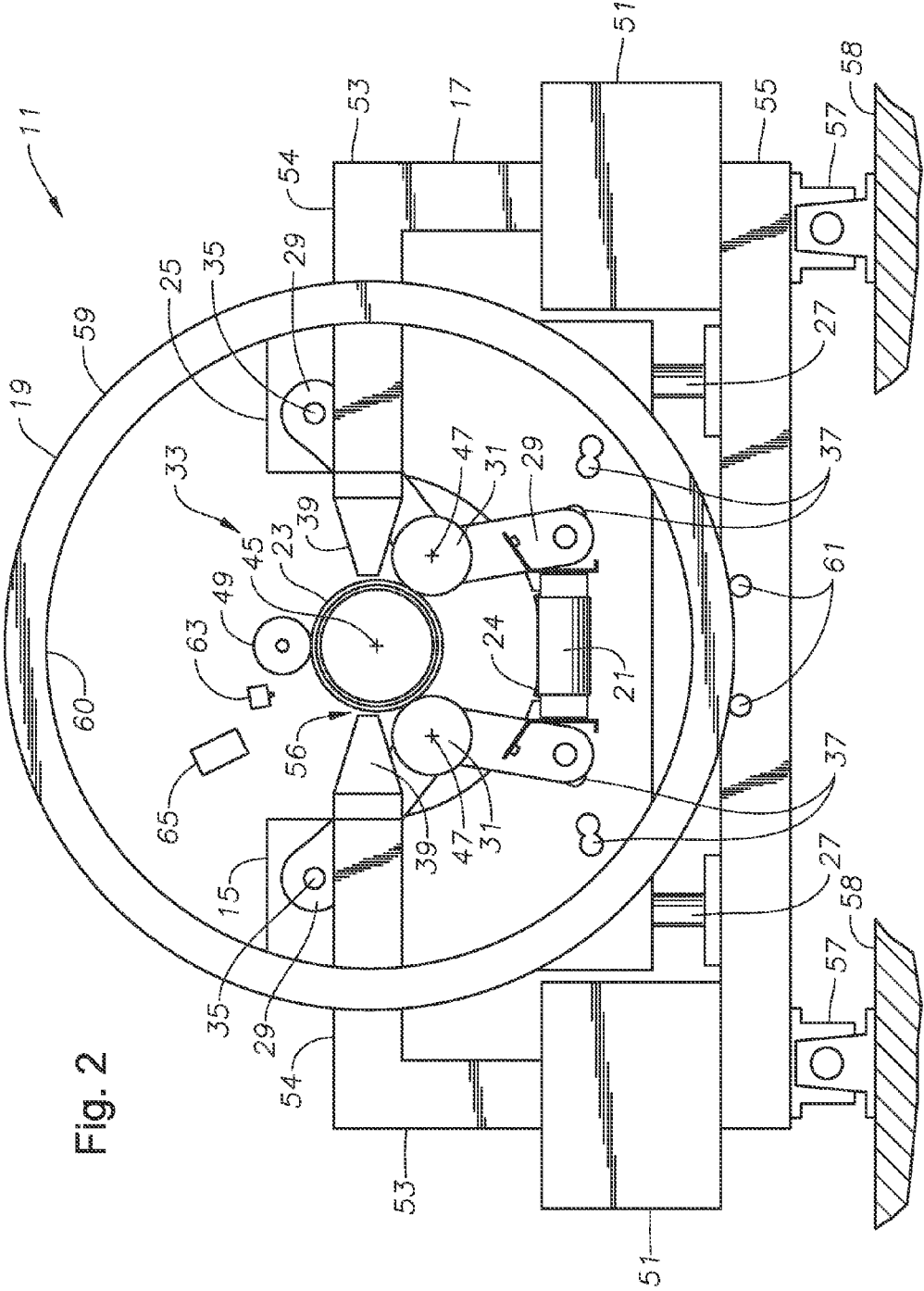
FIG. 2 is a schematic left side elevation view of the inspection station of FIG. 1 having the coupler in an upper position.

Referring to FIG. 2, lifting apparatus 15 includes a lift plate 25, lifts 27, roller mounting brackets 29, and rollers 31. In the illustrated embodiment, two lifts 27 couple to lift plate 25. A person skilled in the art will understand that more or fewer lifts 27 may be used as needed. Lifts 27 further couple to an inspection station frame (not shown) and are configured to raise and lower coupler 23 relative to LFRD 17 from a lower position, shown in FIG. 1 and FIG. 3, to an upper position, shown in FIG. 2. When in the upper position, the exterior surface of coupler 23 will engage a motorized roller 49 during inspection of coupler 23. Lifts 27 may include linear bearing lifts, screw lifts, hydraulic lifts, or the like. In an exemplary embodiment, lifts 27 are automatically operated based on expected operational timing or alternatively based on sensors (not shown) indicating that a coupler or pipe end is positioned and ready to be lifted. Alternatively, lifts 27 may be manually operated. As shown in FIG. 1, each lift 27 includes a rail 28 adapted to be mounted to a body, substantially vertical surface, or the like having sufficient strength to bear the weight of the of lifting apparatus 15 and coupler 23. Each lift 27 may also include a bearing 30 adapted to mount lift plate 25 to each rail 28. Bearings 30 may be motorized to provide locomotive action for lifting apparatus 15. In other embodiments, an external lift may be mounted to bearings 30 or lift plate 25 to provide the necessary force to lift lifting apparatus 15.

Lift plate 25 of FIG. 2 is a plate configured to mount lifts 27 and roller mounting brackets 29. In the exemplary embodiment, lift plate 25 is a planar member substantially normal to an axis of coupler 23. As shown in FIG. 2, lift plate 25 defines an opening 33 configured to allow passage of coupler 23 through lift plate 25. Opening 33 extends inward from an upper edge of lift plate 25. In the illustrated embodiment, opening 33 has a width substantially greater than the diameter of coupler 23, and a rounded lower end. A person skilled in the art will understand that opening 33 may vary in size and shape as needed to permit passage of coupler through lift plate 25 from first conveyor 13. Lift plate 25 further defines upper mounting holes 35, and a plurality of lower mounting holes 37. Roller mounting brackets 29 include suitably shaped brackets configured to position rollers 31 to lift and bear the weight of coupler 23 during inspection. As shown, roller mounting brackets 29 position rollers 31 so that a distance between rollers 31 is less than a diameter of coupler 23. In an exemplary embodiment, when conveyor 13 moves coupler 23 on a carrier 24 proximate to rollers 31, rollers 31 will engage an exterior surface of coupler 23. Lifts 27 will actuate to raise lift plate 25 vertically raising the coupled roller mounting brackets 29 and rollers 31 vertically. When lift plate 25 moves to the upper position shown in FIG. 2, rollers 31 will bear the weight of coupler 23 without also lifting carrier 24. Furthermore, when lifting apparatus 15 raises coupler 23 to the upper position of FIG. 2, a gap between the exterior diameter surface of coupler 23 and an adjacent end of extenders 39 of LFDA 17 is minimized. In an exemplary embodiment, this gap is approximately ¼" or more.

Figure 3:
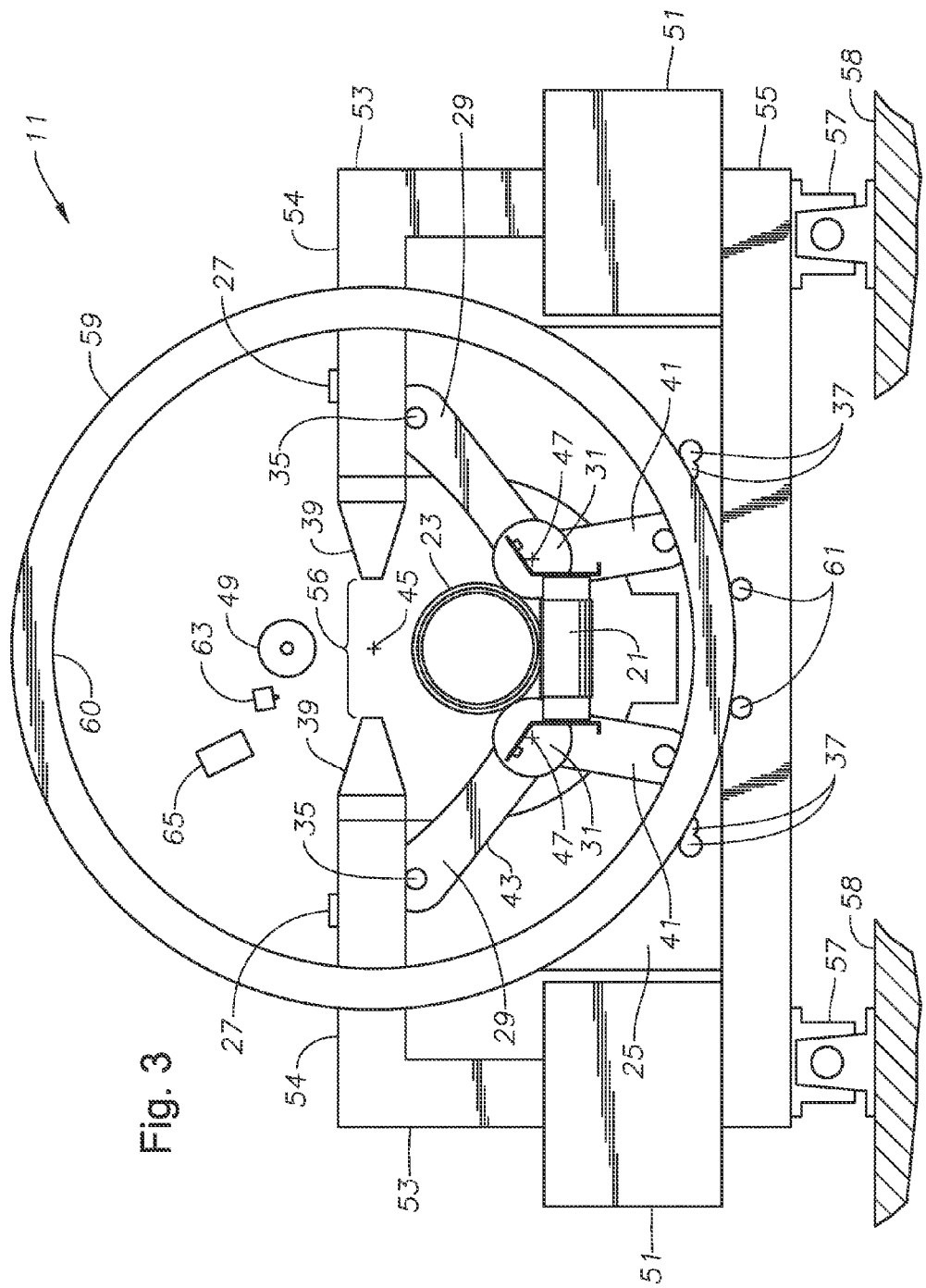
FIG. 3 is a schematic left side elevation view of the inspection station of FIG. 1 having the coupler in the lower.

In the illustrated embodiment, roller mounting brackets 29 each have a lower member 41 (FIG. 3) and an upper member 43 (FIG. 3). Lower member 41 and upper member 43 join at interior ends proximate to a horizontal axis 45 passing through a center of opening 33 so that each roller mounting bracket 29 has L-like shaped with a declined upper leg. A lower end of lower member 41 couples to lift plate 25 with fasteners (not shown) that insert through lower mounting holes 37 in lower member 41 and plate 25 where holes 37 extend generally parallel with axis 45. Lower mounting holes 37 include pre-formed holes positioned such that inspection station 11 may be adjusted to accommodate for various coupler and pipe diameter sizes. Each lower mounting hole 37 corresponds to a particular diameter range of pipe sizes such that when lower member 41 couples to a particular lower mounting hole 37, rollers 31 will be positioned to lift that particular range of coupler sizes from a carrier into the upper position to be inspected. An upper end of upper member 43 (FIG. 3) couples to lift plate 25 with fasteners (not shown) that insert through upper mounting holes 35 in upper member 43 and lift plate 25.

Rollers 31 couple to roller mounting brackets 29 at an end of rollers 31 proximate to lift plate 25. Rollers 31 of FIG. 2 are rotational elements configured to support the weight of coupler 23 while allowing rollers 31 to rotate about an axis 47 passing through a center of each roller 31. Rollers 31 are free spinning rollers configured to allow coupler 23 to rotate on rollers 31 when the coupler 23 is rotated by motorized roller 49.

In the example of FIG. 2, motorized roller 49 is a roller having a cylinder like configuration that is coupled to an internal or external motor (not shown). The motor rotates motorized roller 49 that in turn drives cylindrical or spherical member(s) frictionally engaged to the exterior surface of motorized roller 49. Motorized roller 49 couples to the inspection station frame (not shown) such that, during inspection of coupler 23, an exterior surface of motorized roller 49 will engage the exterior surface of coupler 23, transferring rotational motion of motorized roller 49 to coupler 23, thereby rotating coupler 23. The contact force between the exterior surface of motorized roller 49 and coupler 23 when coupler 23 is in the upper position will be sufficient to overcome any loss of friction between the surfaces caused by wetting of either or both surfaces. Motorized roller 49 may be positioned with an air spring to prevent undesired movement of motorized roller 49 during inspection of coupler 23. Similar to roller mounting brackets 29, motorized roller 49 may be adjusted to accommodate different pipe sizes.

Still referring to FIG. 2, LFDA 17 includes a yoke having coils 51, side circuit elements 53, upper circuit elements 54, base circuit element 55, and moveable rails 57. Optionally, LFDA 17 may include extenders 39. Side, upper, and base circuit elements 53, 54, 55 include a low retentivity iron. As illustrated in FIG. 2, lower ends of side elements 53 perpendicularly join base element 55 at opposing ends of base element 55. Upper ends of side elements 53 perpendicularly join ends of upper circuit elements 54; this embodiment positions upper circuit elements 54 over base circuit element 55. As shown, side circuit elements 53, upper circuit elements 54, and base circuit element 55 have a generally rectangular profile. A person skilled in the art will understand that side circuit elements 53, upper circuit elements 54, and base circuit element 55 may have any suitable profile, such as a cylindrical or triangular profile, provided elements 53, 54 and 55 operate as described herein. Non-joined ends of upper circuit elements 54 are shown separated by a gap 56. The gap 56 may be approximately equal to the exterior diameter of coupler 23. In an exemplary embodiment, when coupler 23 is raised into the upper position, coupler 23 can substantially fill gap 56. In one example, a ¼" gap exists between the end of each upper circuit element 54 end and the exterior surface of coupler 23. Optionally, the gaps between opposite ends of upper circuit elements 54 and the exterior diameter surface of coupler 23 are equal. Extenders 39 may be coupled to ends of upper circuit element 54 to close narrow gap 56 to the appropriate distance.

Coils 51 include wire coils wound around side circuit elements 53. Coils 51 may be coupled to a DC power supply (not shown), such as a Sorensen XFR Series, Xantrex Technology XFR300-9 series, or the like. Current from the power supply to coils 51 can induce a magnetic field in circuit elements 53, 54, 55 which are magnetically coupled to coils 51. When coupler 23 is lifted to the upper position filling gap 56, the magnetic field completes a magnetic circuit through coupler 23 by passing circumferentially through a wall of coupler 23. In an exemplary embodiment, coils 51 each include 100 turns of wire in each coil sized such that, when powered, coils 51 produce approximately 5,000 ampere turns of magnetic motive force. In another exemplary embodiment, coils 51 each include approximately 2500 turns of wire in each coil sized such that, when powered, coils 51 produce approximately 10,000 ampere turns of magnetic motive force.

Moveable rails 57 couple to base circuit element 55 through suitable bearings and further couple to the inspection station frame or a substantially planar horizontal surface 58. Moveable rails 57 are configured to move ends of upper circuit elements 54 horizontally the length of coupler 23 during inspection, exposing the entire length of coupler 23 to the circumferential magnetic field produced by LFDA 17. Moveable rails 57 may include hydraulically actuated pistons, screw type devices, linear bearing devices, or the like that are actuable to move the base circuit element 55, and the coupled side and upper circuit elements 53, 54 along the length of rails 57. Movement of LFDA 17 along rails 57 may be controlled based on expected inspection process time, sensors (not shown) located within inspection station 11, or by manual operation.

Continuing to refer to FIGS. 2 and 3, TFDA 19 includes an electromagnetic ring 59 coaxial with axis 45. Electromagnetic ring 59 has a wire coil (not shown) wound coaxial with axis 45 within a housing 60. The wire coil of electromagnetic ring 59 couples to a DC power supply (not shown). The DC power supply, such as a Sorensen XFR Series, Xantrex Technology XFR300-9 series, or the like, is configured to supply a current to the wire coil of electromagnetic ring 59 inducing a magnetic field configured to pass longitudinally through coupler 23 during inspection. In addition, electromagnetic ring 59 may produce approximately 5,000-10,000 ampere turns of magnetic motive force. In alternative embodiments, electromagnetic ring 59 will be hinged and offset from axis 45 such that electromagnetic ring 59 may variably move radially closer to and away from coupler 23.

The power supplies to LFDA 17 and TFDA 19 may be one unit configured to alternately power LFDA 17 and TFDA 19. Alternatively, the power supplies to LFDA 17 and TFDA 19 may comprise multiple units configured to variably operate to power LDFA 17 and TFDA 19. A person skilled in the art will understand that any suitable electrical configuration capable of supplying power to LFDA 17 and TFDA 19 in the manner described below are contemplated and included in the disclosed embodiments.

Housing 60 of FIG. 2 couples to base circuit element 55 by ring couplers 61. In the illustrated embodiments, ring couplers 61 are cylindrical members that are mounted within corresponding bores formed in base circuit element 55. Housing 60 may be secured to upper portions of ring couplers 61 by any suitable manner, such as by welding, fasteners or the like. A person skilled in the art will understand that housing 60 may be secured to base circuit element 55 by any suitable manner and some embodiments may not use ring couplers 61. Similar to LFDA 17, TFDA 19 may move along rails 57 such that the entire length of coupler 23 will pass through an interior of electromagnetic ring 59 during inspection of coupler 23. This allows the entirety of coupler 23 to be exposed to the magnetic field at the same intensity at some point during an inspection process described below.

Still referring to FIG. 2, a spray bar 63 is shown positioned, in any suitable manner, proximate to motorized roller 63. Spray bar 63 includes an apparatus connected to a fluid circulation system and configured to spray a fluid onto an exterior surface of coupler 23 during inspection. Spray bar 63 may be coupled to the inspection frame, or alternatively positioned by an operator of inspection station 11. The fluid passed through spray bar 63 and onto the surface of coupler 23 includes a magnetic particle inspection material (MPI) mixed with water or other fluids as needed. In an example, the MPI includes a ferrous powder coated with a fluorescing substance. In natural light, the MPI is not discernable to the naked eye within the fluid; however, when exposed to an ultraviolet light, the MPI fluoresces and is visible to the naked eye. Inspection station 11 may include a sump (not shown) positioned beneath rollers 31 and configured to collect and recirculate the MPI fluid passing through spray bar 63. In addition, an operator may have a handheld spray device that is moveable to spray an interior of coupler 23 with the MPI fluid. A person skilled in the art will understand that the MPI may be used without an associated fluid.

At least one ultraviolet light source 65 may be positioned to expose the exterior surface of coupler 23 to an ultraviolet light during inspection. Ultraviolet light source 65 may couple to the inspection frame (not shown) or alternatively may be handheld. In addition, an operator may have a handheld ultra violet light that is moveable to expose the interior of coupler 23 to ultraviolet light.

Figure 4:
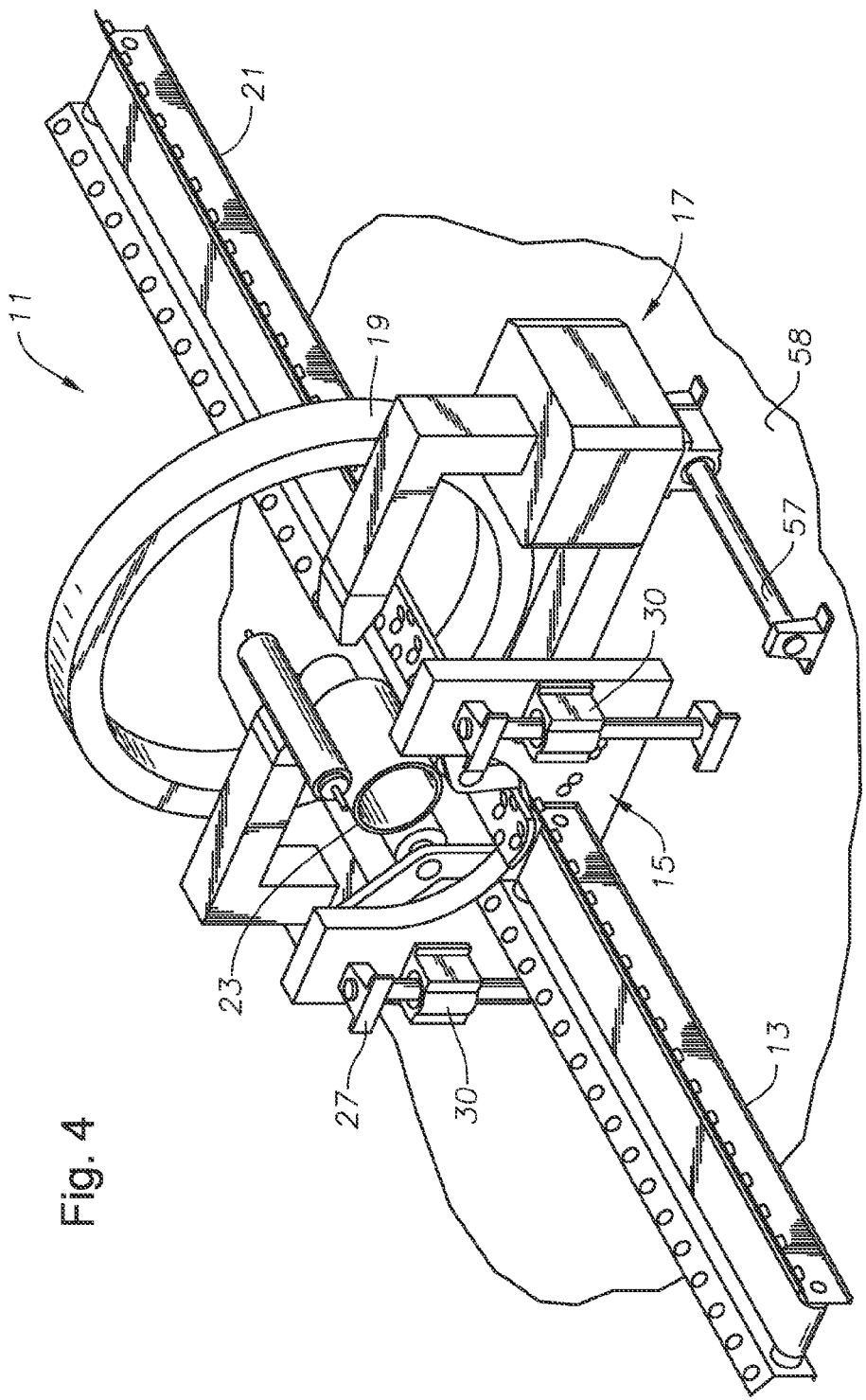
FIG. 4 is a schematic perspective view of the inspection station of FIG. 1 having the coupler in the upper position.

In one non-limiting example of operation of an inspection process, the conveyor 13 moves coupler 23 proximate to lifting apparatus 15 as shown in FIG. 1. Lifting apparatus 15 is in the lower position as shown FIG. 1 and FIG. 3. Conveyor 13 moves coupler 23 until coupler 23 is positioned over rollers 31. Lifting apparatus 15 lifts coupler 23 on rollers 31 so the exterior surface of coupler 23 engages motorized roller 49 as shown in FIG. 2 and FIG. 4. The motor coupled to motorized roller 49 rotates motorized roller 49, and the frictional contact between motorized roller 49 and coupler 23 rotates coupler 23 in rollers 31 with rotation of motorized roller 49. Coupler 23 continues to rotate throughout the entire inspection process. An operator may optionally turn on spray bar 63 to maintain the MPI fluid spray on the exterior surface of coupler 23 with the MPI fluid for the duration of the inspection process. Alternatively, spray bar 63 may operate continuously while inspection station 11 is operated.

LFDA 17 is powered and a current is applied to coils 51. This may occur automatically, or alternatively in response to input from an operator. The current passing through coils 51 induces a magnetic field in circuit elements 53, 54, and 55. As shown in FIG. 5, the magnetic flux lines 67 represent a magnetic field completing a magnetic circuit by passing from one extender 39 circumferentially around the wall of coupler 23 and into the other extender 39. LFDA 17 moves the length of coupler 23 along rails 57, as shown in FIG. 4A, while coupler 23 continues to rotate, subjecting the entire wall of coupler 23 to the magnetic circuit.

Figure 5:
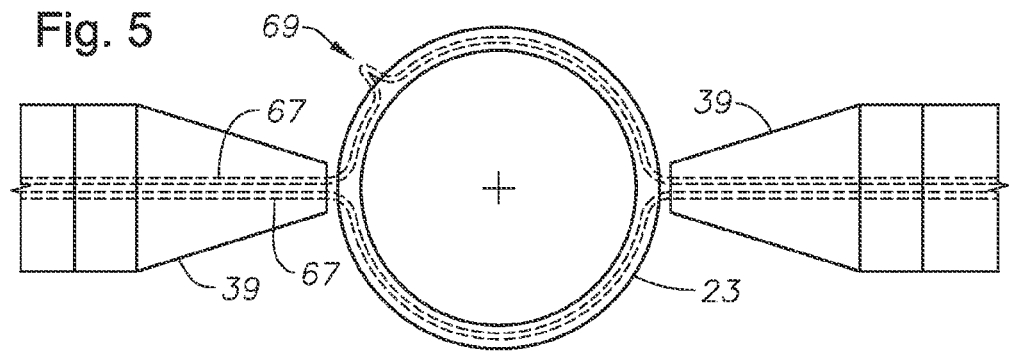
FIG. 5 is a schematic sectional view of the coupler of FIG. 1, illustrating an example of a circumferential magnetic field.
Figure 6:
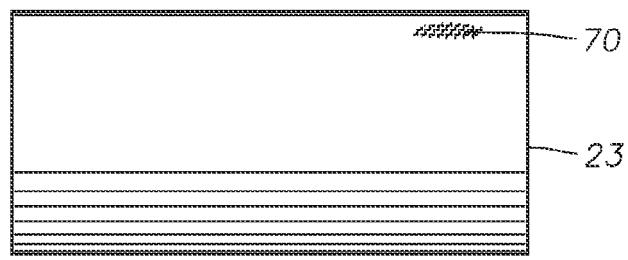
FIG. 6 is a schematic view of the surface of the coupler of FIG. 1, illustrating an example of a magnetic particle inspection (MPI) congregation at a longitudinal flaw.

An operator may visually monitor the surface of coupler 23. In an example, at areas where coupler 23 is free of flaws, flux lines 67 will pass through coupler 23 relatively uniformly, as shown by flux lines 67 passing through the lower half of coupler 23 in FIG. 5. In an example, at areas where coupler 23 has a flaw or anomaly perpendicular to the circumferential magnetic field represented by flux lines 67, the permeability, the measure of how easily magnetic flux passes through a material, of coupler 23 will change, causing magnetic flux 67 to leak out of the surface of coupler 23 as shown at leak 69. Leak 69 may be an area where a flaw in coupler 23 forces flux lines 67 to breach the surface of coupler 23. At these areas, the magnetic field will exert a magnetic force on the MPI of the MPI fluid, congregating the MPI at the anomaly and conforming it to the shape of the leak caused by the flaw. Typically, this will be the same approximate size and shape as the flaw. The ultraviolet light 65 shined on the exterior surface of coupler 23 will illuminate a congregated MPI 70. The operator can then see MPI congregation 70 as a colored spot on the surface of coupler 23 and note that there is a longitudinal anomaly in coupler 23, as shown in FIG. 6.

Figure 7:
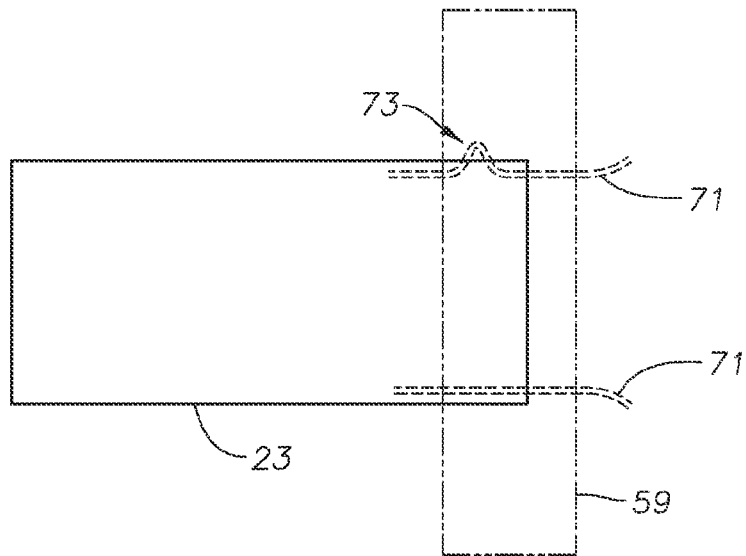
FIG. 7 is a schematic sectional view of the coupler of FIG. 1, illustrating an example of a longitudinal magnetic field.

In an example, where LFDA 17 has traversed the entire length of coupler 23, power to LFDA 17 can be switched off, removing the circumferential magnetic field from coupler 23. While coupler 23 continues to rotate, power to TFDA 19 can be switched on. Powering TFDA 19 passes current through the coil of electromagnetic ring 59. In response, the coil of electromagnetic ring 59 can induce a magnetic field that will pass longitudinally through coupler 23 as shown in FIG. 7 by flux lines 71. TFDA 19 can be moved the length of coupler 23 along rails 57, as shown in FIG. 4A, subjecting the entire length of coupler 23 to a magnetic field of the same intensity at some point during the inspection process.

Figure 4A:
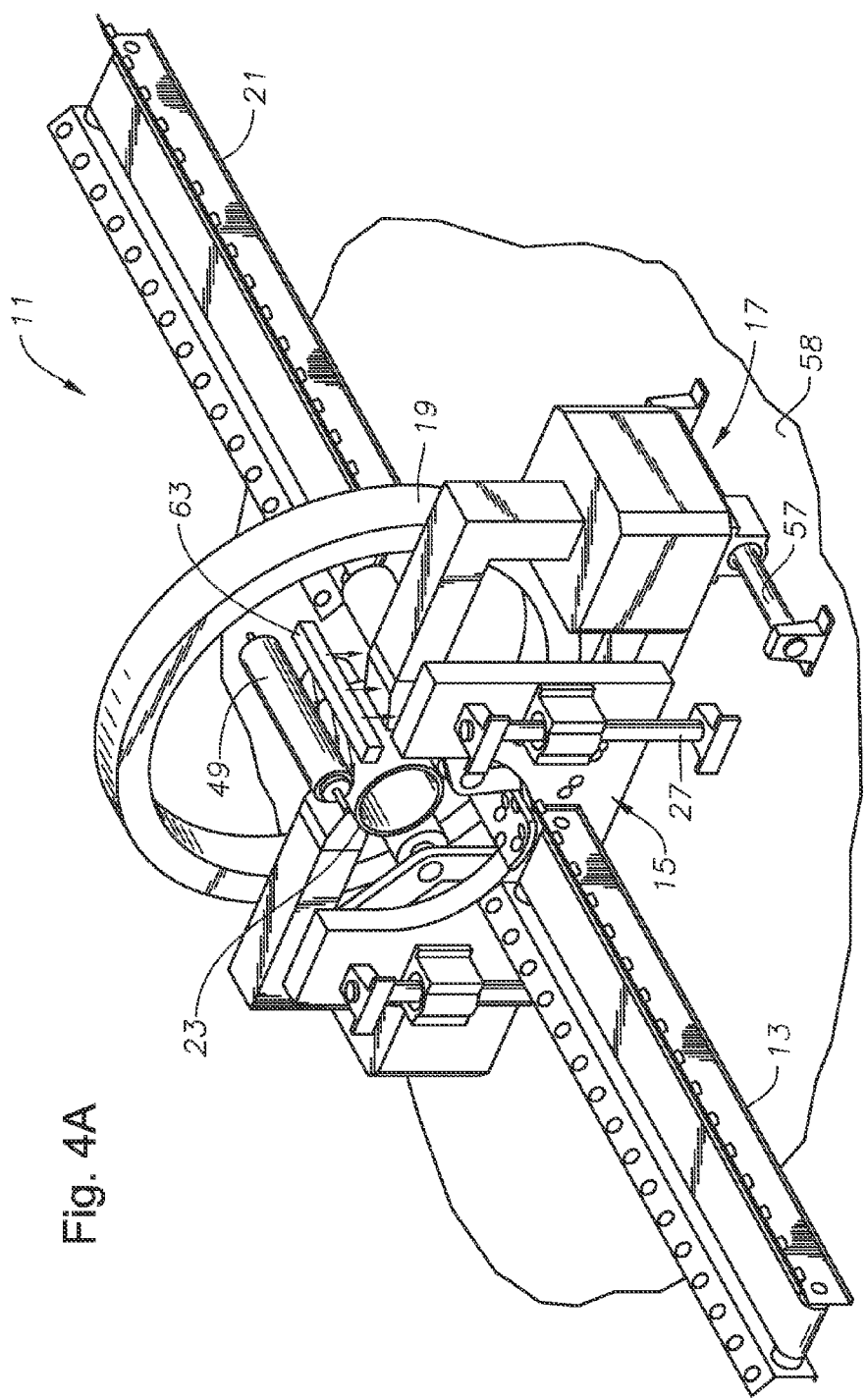
FIG. 4A is a schematic perspective view of the inspection station of FIG. 1 having the coupler in the upper position and a magnetic inspection apparatus moved proximate to the coupler.
Figure 8:
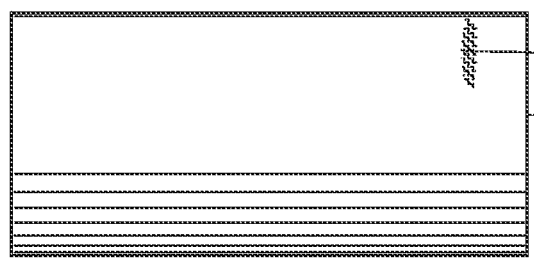
FIG. 8 is a schematic view of the surface of the coupler of FIG. 1, illustrating an example of an MPI congregation at a transverse flaw.

Optionally, spray bar 63 may spray MPI fluid on the exterior surface of coupler 23 as shown by the arrows of FIG. 4A while motorized roller 49 rotates coupler 23 and an operator monitors the surface of coupler 23. At areas where coupler 23 is free of flaws, flux lines 71 pass through coupler 23 relatively uniformly, as shown by flux lines 71 passing through the lower half of coupler 23 in FIG. 7. At areas where coupler 23 has a flaw or anomaly perpendicular to the magnetic field represented by flux lines 71, the permeability, the measure of how easily magnetic flux passes through a material, of coupler 23 will change, causing magnetic flux 71 to leak out of the surface of coupler 23 as shown at leak 73. At these areas, the magnetic field will exert a magnetic force on the MPI of the MPI fluid, congregating the MPI at the anomaly and conforming it to the shape of the leak caused by the flaw. Typically, this may be the same approximate size and shape as the flaw. The ultraviolet light 65 shined on the exterior surface of coupler 23 illuminates a congregated MPI 75. The operator can identify MPI congregation 75 as a colored spot on the surface of coupler 23 and note that there is a transverse anomaly in coupler 23, as shown in FIG. 8.

TFDA 19 may make a second pass across the horizontal length of coupler 23. During this pass, the operator can use the handheld fluid sprayer and handheld ultraviolet light to first spray the interior of coupler 23 with the MPI fluid to expose the interior surface to the ultraviolet light, thereby visually inspecting the interior surface of coupler 23. As described above, at locations of anomalies, flux leakage will occur attracting MPI particles in the MPI fluid. The operator may visually see this when the MPI fluid is exposed to the handheld ultraviolet light. The operator can note any transverse anomalies on the interior surface of coupler 23.

After, TFDA 19 has traversed the entire length of coupler 23, power to TFDA 19 may be switched off, removing the longitudinal magnetic field from coupler 23. Next, while coupler 23 continues to rotate, power to LFDA 17 may be switched on, again inducing a circumferential magnetic field in coupler 23 as shown in FIG. 5. Moving LFDA 17 the length of coupler 23 along rails 57 induces a circumferential magnetic field in coupler 23 along the entire length of coupler 23. During this pass, the operator, instead of visually inspecting the exterior surface of coupler 23, can use the handheld fluid sprayer and handheld ultraviolet light to first spray the interior of coupler 23 with the MPI fluid, and then expose the interior surface to the ultraviolet light, thereby visually inspecting the interior surface of coupler 23. As described above, at locations of anomalies, flux leakage will occur, attracting MPI particles in the MPI fluid. The operator will visually see this when the MPI fluid is exposed to the handheld ultraviolet light. The operator will then note any longitudinal anomalies on the interior surface of coupler 23.

In this manner, both the interior and exterior of coupler 23 may be inspected for both transverse and longitudinal flaws as well as helical flaws having both transverse and longitudinal components in one machine. This overcomes prior art problems that prevented inspection of pipe ends and couplers. For example, the disclosed embodiments provide a pipe inspection apparatus capable of inspecting couplers and pipe ends and detecting flaws in both the transverse and longitudinal directions without the necessity of electronic sensors that are dependent on the position of the coil relative to the sensor and inspected tubular member. In addition, the disclosed embodiments do not suffer from interference between the longitudinal and circumferential magnetic fields at pipe ends that prevented inspection of both transverse and longitudinal flaws in prior art devices.

Furthermore, the system and method uses active magnetic fields for inspection, rather than residual fields to enhance the detection of anomalies. The use of active fields allow the disclosed embodiments to accomplish this while preventing the longitudinal magnetic field from overcoming the circumferential magnetic field prior to inspection. Methods relying on residual magnetic fields are often unable to detect longitudinal flaws due to this problem. In the event that the coupler or pipe end becomes magnetized, TFDA 17 may be powered with a reverse polarity to remove the magnetization of the coupler or pipe end. Thus, the inspection station may also serve as a demagnetizer, reducing the need for manipulating the coupler or pipe into a separate demagnetization station, reducing the time and cost necessary to properly inspect the pipe ends.

Figure 9:
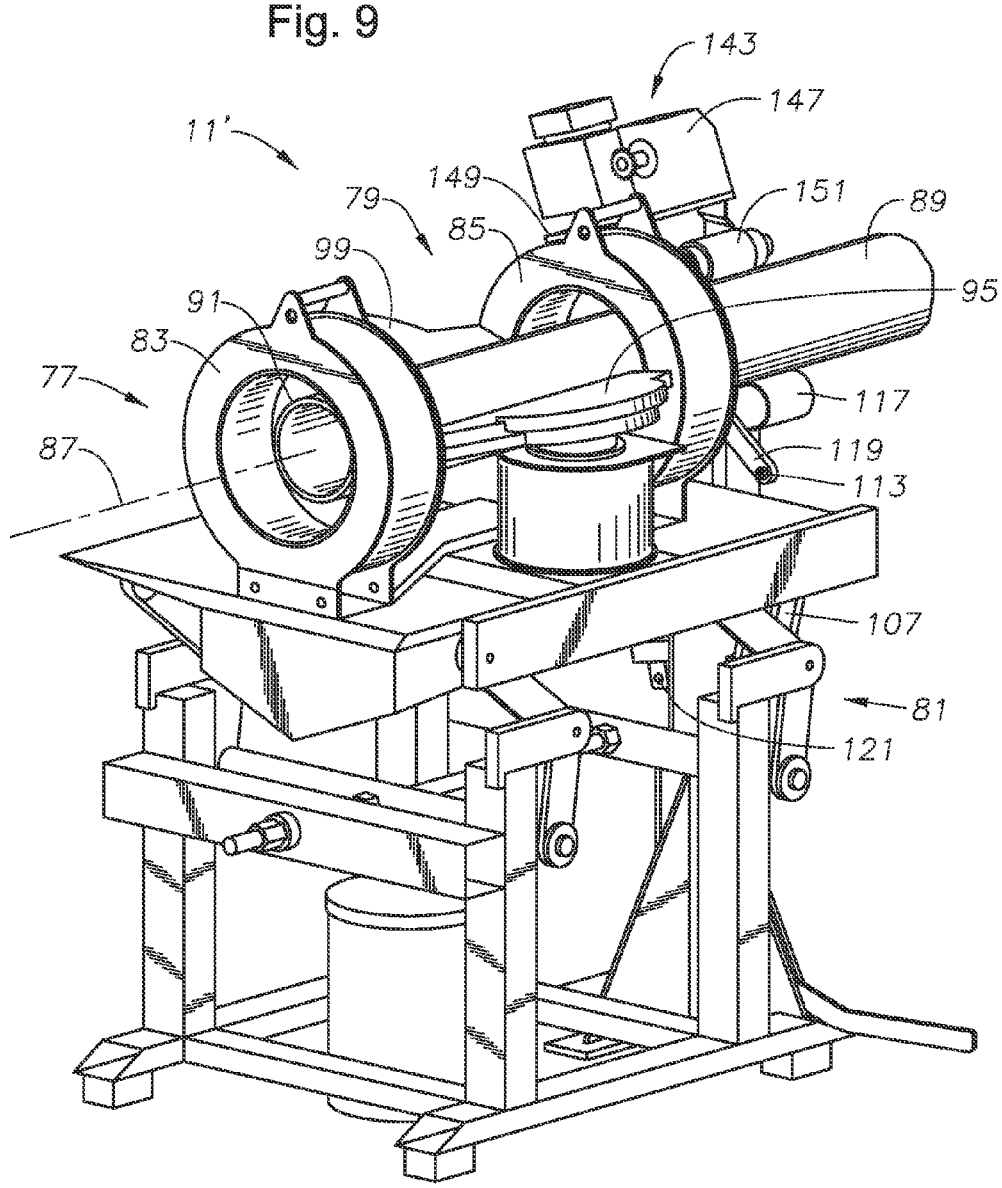
FIG. 9 is a perspective view of an alternative inspection station in accordance with an embodiment of the present invention.

An alternative example of a magnetic ends area inspection station 11' for inspecting tubular member ends and detecting anomalies is shown in FIGS. 9-13. Inspection station 11' may include all the elements of inspection station 11 described above with respect to FIGS. 1-8, modified as described in more detail below. Referring now to FIG. 9, the example of inspection station 11' includes a transverse flaw detection apparatus (TFDA) 77 and a longitudinal flaw detection apparatus (LFDA) 79 securely mounted to an inspection station frame assembly 81. TFDA 77 and LFDA 79 may operate in a manner similar to TFDA 19 and LFDA 17, respectively, of FIGS. 1-4.

TFDA 77 of FIG. 9 includes a first electromagnetic ring 83 and a second electromagnetic ring 85 shown coaxial with first electromagnetic ring 83. Both the first electromagnetic ring 83 and the second electromagnetic ring 85 are mounted to the inspection station frame assembly 81 so that the first and second electromagnetic rings 83, 85 are coaxial with an axis 87 of a tubular member 89, such as the illustrated pipe. First and second electromagnetic rings 83, 85 include a wire coil (not shown) wound coaxial with axis 87 within a housing. The wire coil of each electromagnetic ring 83, 85 couples to a DC power supply (not shown). The DC power supply, such as a Sorensen XFR Series, Xantrex Technology XFR300-9 series, or the like is configured to supply a current to the wire coil of electromagnetic rings 83, 85 to induce a magnetic field configured to pass longitudinally through an end 91 of tubular member 89. First and second electromagnetic rings 83, 85 are adapted to generate a longitudinal magnetic field that passes through end 91 parallel to axis 87. By using both first electromagnetic ring 83 and second electromagnetic ring 85 to generate the longitudinal field, the longitudinal portion of the electromagnetic field 84 (FIG. 9A) may be extended beyond end 91 of tubular member 89, thus eliminating end flux leakage of issues of the prior art. This increases accuracy of the transverse flaw detection process and decreases deviations of the magnetic field caused by distance from the magnetic coils.

Figure 11:
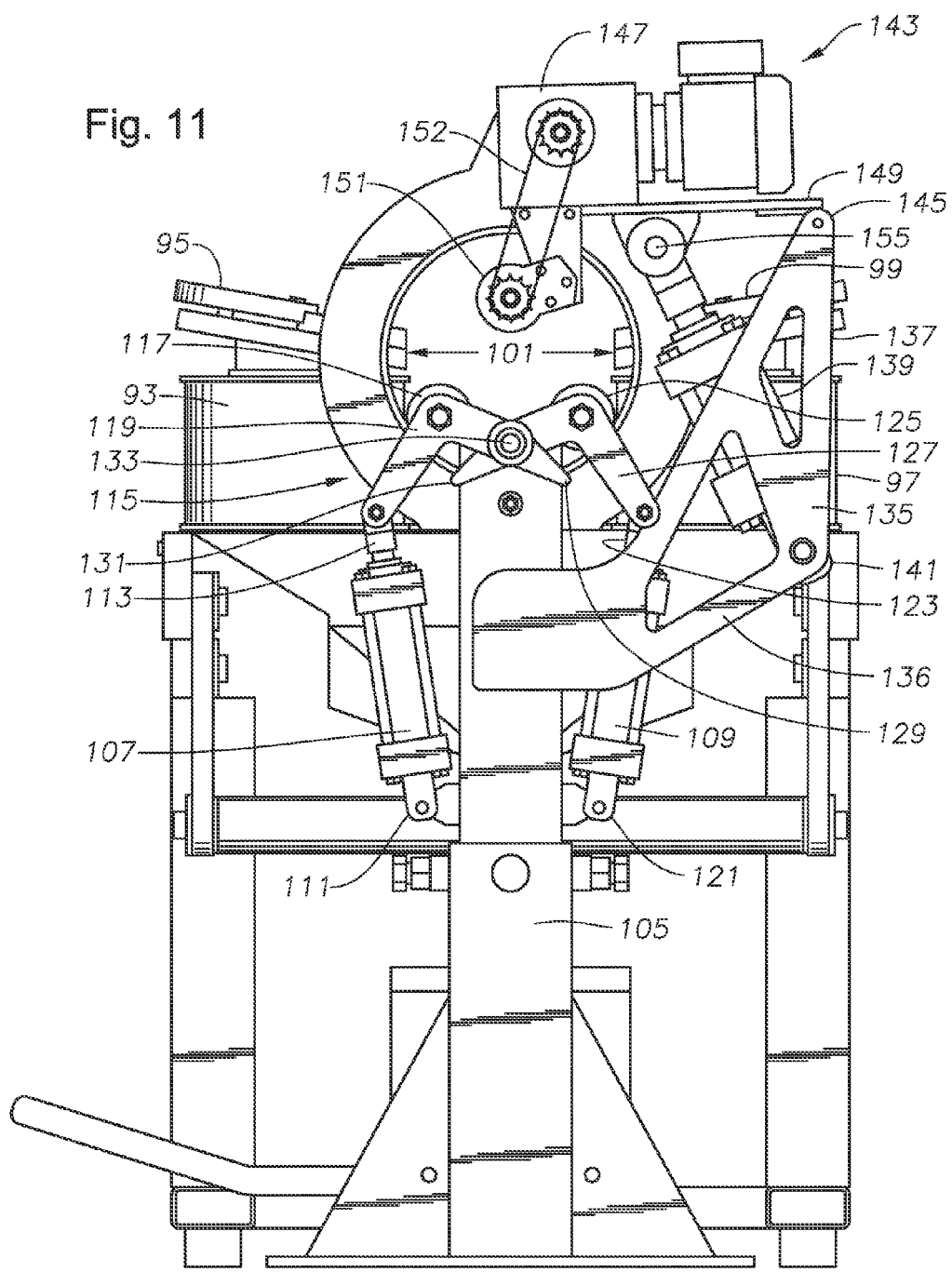
FIG. 11 is a rear elevation view of the inspection station of FIG. 9.
Figure 12:
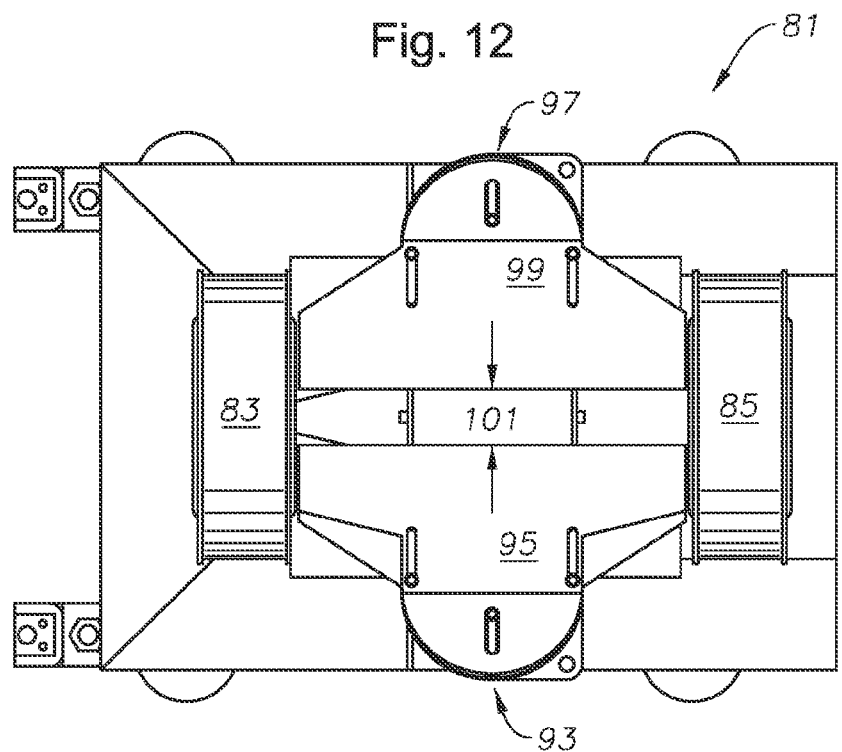
FIG. 12 is a top plan view of the inspection station of FIG. 9.

In the alternative embodiment, LFDA 79 includes a first magnetic coil 93 magnetically coupled to a first magnetic pole 95 and a second magnetic coil 97 (FIG. 11) magnetically coupled to a second magnetic pole 99 (FIG. 12). A person skilled in the art will understand that second magnetic coil 97 and second magnetic pole 99 will operate in a manner similar to that of first magnetic coil 93 and first magnetic pole 95 described in more detail below. In the illustrated embodiment of FIGS. 9-13, second magnetic coil 97 and second magnetic pole 99 will mirror first magnetic coil 93 and first magnetic pole 95 across inspection station frame assembly 81. First and second magnetic poles 95, 99 are adapted to form a magnetic circuit across a gap 101 (FIG. 12) that spans between the first magnetic pole 95 and the second magnetic pole 99. First and second magnetic poles 95, 99 have a magnetic polarization when power is supplied to the first magnetic coil 93 and the second magnetic coil 97. In an exemplary embodiment, the magnetic poles 95, 99 may be oppositely polarized so that a magnetic circuit may be completed through end 91 of tubular member 89 when tubular member 89 is positioned within magnetic ends area inspection station 11' as illustrated above with respect to ends area inspection station 11 of FIG. 5 and further illustrated by flux lines 90 in FIG. 9B. In an example, when end 91 is inserted between first magnetic pole 95 and second magnetic pole 97, and power is supplied to first magnetic coil 93 and second magnetic coil 97, the magnetic coils 93, 97 magnetically polarize their respective magnetic poles 95, 99 with opposite polarization, generating a magnetic field across gap 101 through end 91 of tubular member 89.

In one example embodiment, first magnetic pole 93 and second magnetic pole 97 have a length substantially equivalent to the distance between first electromagnetic ring 83 and second electromagnetic ring 85, as shown in FIG. 12, permitting the circumferential magnetic field 90 to be passed through the entire length of end 91 at the same time as shown in FIG. 9B. This will increase the speed at which end 91 of tubular member 89 may be inspected. In an exemplary embodiment, this length is approximately twenty-four inches. A person skilled in the art will understand that this length may vary depending on the size of tubular member 89. Each tubular member 89 may have an end 91 with a different length. End 91 will correspond to a portion of tubular member 89 that experiences undesirable flux leakage when the remainder of tubular member 89 is inspected.

A person skilled in the art will understand that inspection station 11' will use the MPI apparatus and generally operate as inspection station 11 described in more detail above with respect to FIGS. 1-8. The modifications discussed herein provide for more efficient and accurate inspection of end 91. The modifications of inspection station 11' further reduce the effects of flux leakage near a terminus of end 91 and provide for inspection of the entirety of end 91 without requiring translation of LFDA 77 and TFDA 79 as with LFDA 17 and TFDA 19 described above.

Figure 10:
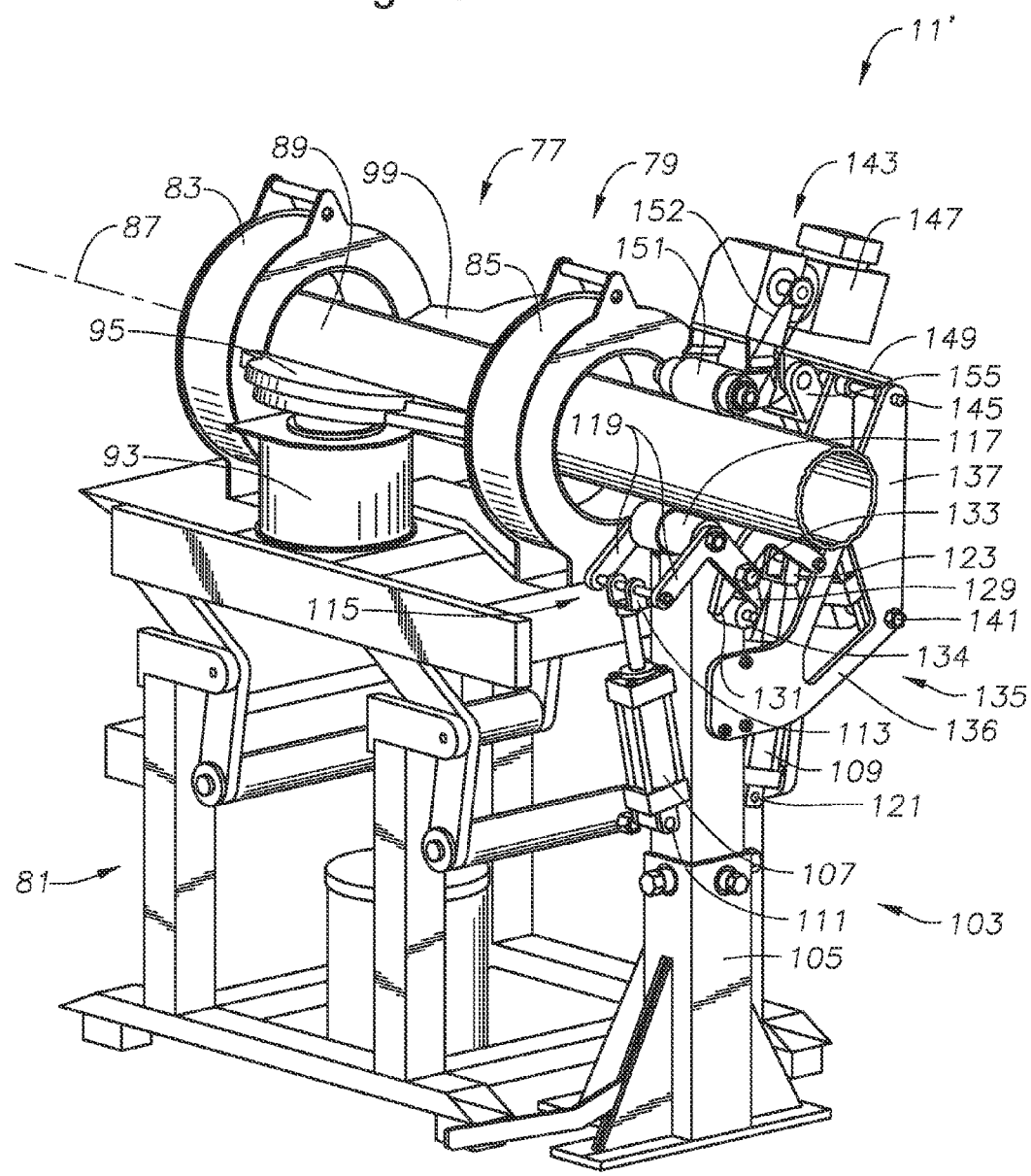
FIG. 10 is an alternative perspective view of the inspection station of FIG. 9.

Inspection station 11' includes a clamping stand 103 (FIG. 10) positioned closely adjacent to inspection station frame assembly 81. In the illustrated embodiment, tubular member 89 is supported within inspection station 11' by clamping stand 103. Clamping stand 103 includes a vertical center support beam 105, a first compensating piston 107, and a second compensating piston 109. As illustrated, center support beam 105 may have two components allowing for vertical adjustment to increase a height of center support beam 105. First compensating piston 107 has a lower end 111 mounted to support beam 105 and an upper end 113 mounted to an exterior end of a compensating roller bracket assembly 115 as shown in FIGS. 10 and 11. Compensating roller bracket assembly 115 includes a first roller 117 supported between a pair of L-shaped brackets 119. First roller 117 is mounted on a roller axle (not shown) extending between elbows of the L-shaped brackets 119. Upper end 113 mounts to a piston axle extending between exterior ends of the L-shaped brackets 119. First roller 117 and upper end 113 may rotate on their supportive axles.

Similarly, second compensating piston 109 has a lower end 121 mounted to support beam 105 on an opposite side of support beam 105 and vertically adjacent to lower end 111 of first compensating piston 107. Second compensating piston 109 has an upper end 123 mounted to an exterior end of compensating roller bracket assembly 115 opposite the first compensating piston 107. Compensating roller bracket assembly 115 includes a second roller 125 supported between a pair of L-shaped brackets 127. Second roller 125 is mounted on a roller axle (not shown) extending between elbows of the L-shaped brackets 127. Upper end 123 mounts to a piston axle extending between exterior ends of the L-shaped brackets 127. Second roller 125 and upper end 123 may rotate on their supportive roller axles.

Interior ends 129, 131 of L-shaped brackets 119, 127, respectively, are supported by an axle 133 joining the interior ends 129, 131 of L-shaped brackets 119, 127 and extending through an upper end of the support beam 105. L-shaped brackets 119, 127 may pivot about axle 133 so that exterior ends coupled to the upper ends 113, 123 of first compensating piston 107 and second compensating piston 109 can move in a generally vertical direction in response to actuation of first compensating piston 107 and second compensating piston 109, as described in more detail below. Portions of interior ends 129, 131 extend beyond axle 133 and contact a selectable limitation knob 134 that limits rotation of the L-shaped brackets 119, 127 so that the first roller 117 and the second roller 125 may not contact one another. Limitation knob 134 may be any suitable size selected to maintain a preselected distance between first roller 117 and second roller 125. For example, limitation knob 134 may be removed and replaced with a limitation knob 134 having different diameter. This will change the point of contact between interior ends 129, 131 and limitation knob 134 to set a different limitation distance between first roller 117 and second roller 125.

A pair of upwardly extending brackets 135 mount to support beam 105 below knob 134 and extend laterally a first distance away from the support beam 105 in the direction of the second compensating piston 109. The upwardly extending brackets 135 include an upwardly extending portion 137. A clamping piston 139 (FIG. 11) has a lower end 141 mounted to a lower clamping piston axle extending between the upwardly extending brackets 135 at the union of the upwardly extending portion 137 with a laterally extending portion 136 of each upwardly extending bracket 135. A motorized roller assembly 143 mounts to an axle between exterior ends 145 of the upwardly extending portion 137. Motorized roller assembly 143 may rotate about the axle extending between exterior ends 145. Motorized roller assembly 143 includes a motor portion 147 positioned on a plate member 149. Plate member 149 has a first end secured to the axle extending between the exterior ends 145 of the upwardly extending portion 137, and a second end having a chain driven roller 151 mounted thereon. The chain driven roller 151 depends toward support member 105 and a motor portion 153 is positioned on the plate member 149. A chain 152 may extend between the motor portion 153 and the chain driven roller 151 to rotate the chain driven roller 151 on a motorized roller axle. In the illustrated embodiment, the chain driven roller 151 can be rotated by the motor portion 147 and will in turn rotate the tubular member 89 as described in more detail below.

Referring now to FIG. 11, clamping piston 139 has an upper end 155 mounted to plate member 149. Clamping piston 139 will be adapted to exert a force on plate member 149 that pulls plate member 149 toward support member 105 to pivot motorized roller assembly 143 about exterior ends 145. Tubular members 89 can be moved into position in inspection station 11' by passing tubular member 89 between first roller 117 and second roller 125 and chain driven roller 151. End 91 passes through the first and second electromagnetic rings 83, 85 and is positioned between the first pole 95 and the second pole 99. Compensating pistons 107, 109 actuate to rotate the respective L-shaped brackets 119, 127 so that the interior ends 129, 137 contact upper portions of the limitation knob 134, thereby maintaining a minimum distance between the first roller 117 and the second roller 125. In the illustrated embodiment, the first roller 117 and the second roller 125 contact an outer surface of tubular member 89 so that the first roller 117 and the second roller 125 bear the weight of tubular member 89. Clamping piston 139 will be actuated to pull the chain driven roller 151 into contact with the outer surface of tubular member 89 and exert a clamping force on tubular member 89 against first roller 117 and second roller 125. Motor portion 153 may operate to drive chain driven roller 151 which will then rotate tubular member 89.

Figure 14:
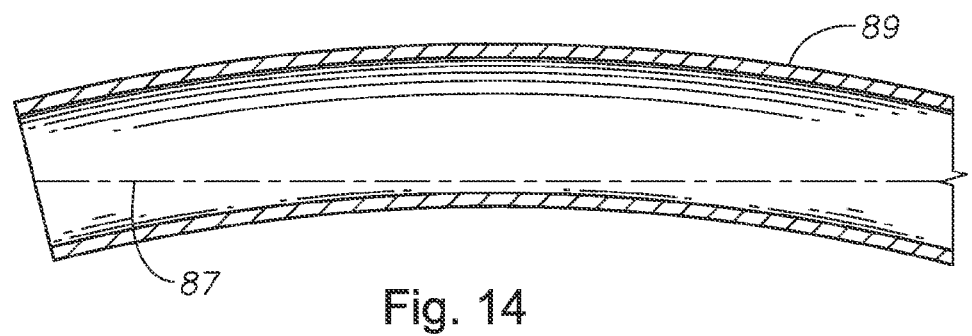
FIGS. 14 and 15 are schematic representations of a tubular member for inspection in the alternative inspection assembly of FIGS. 9-13.
Figure 15:
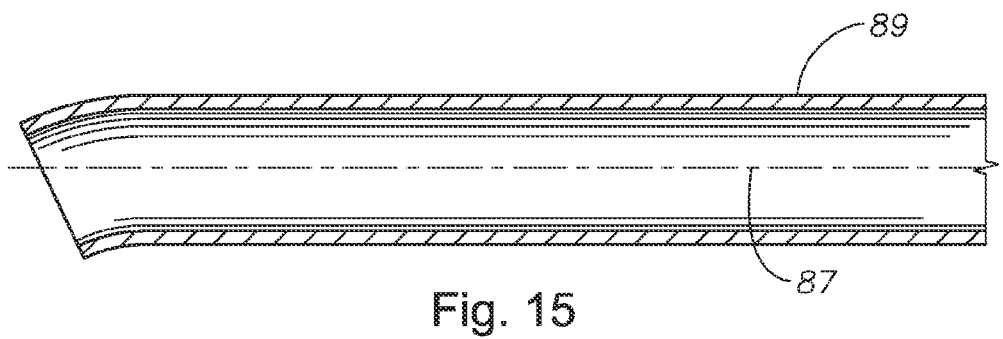
Figure 13:
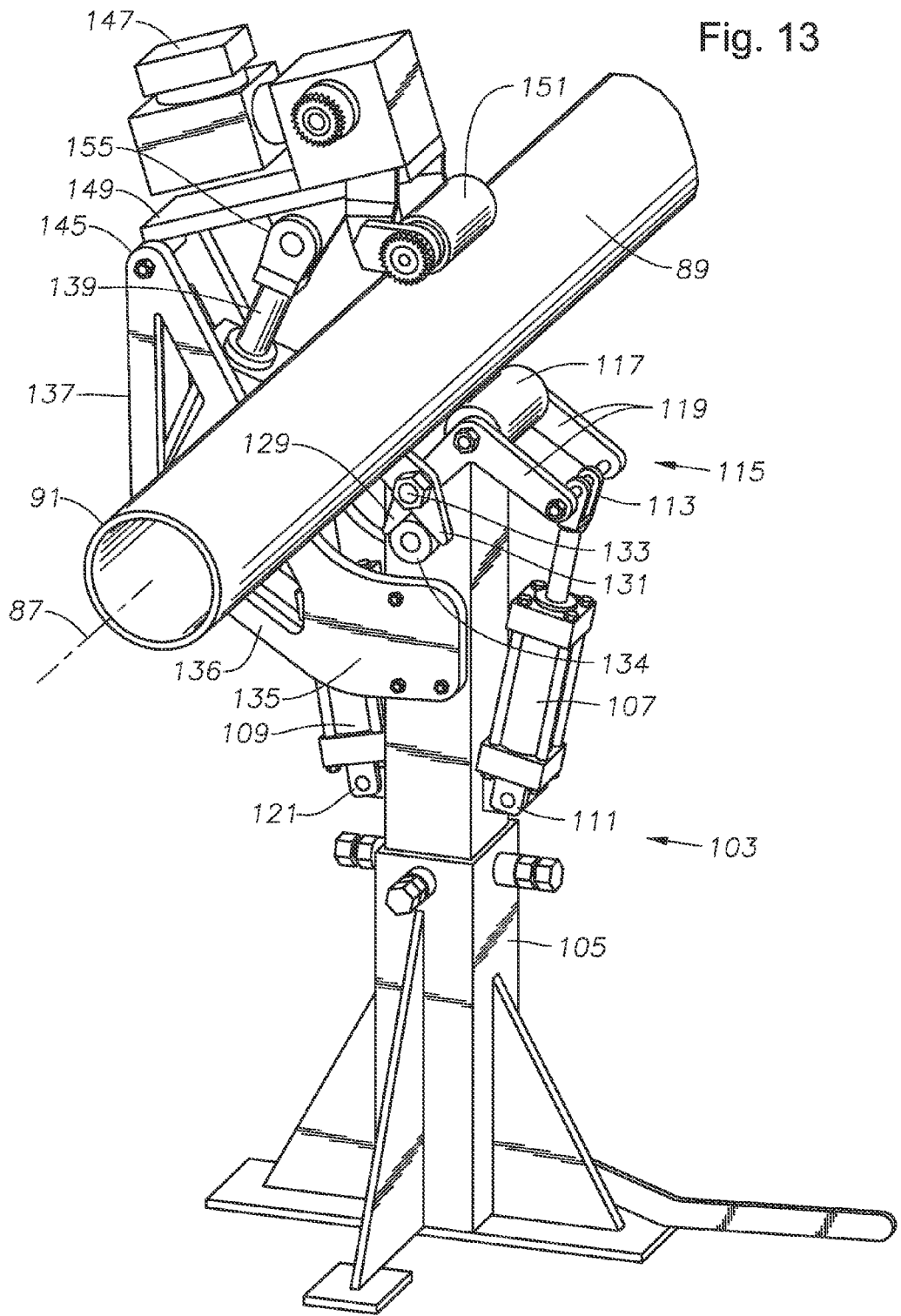
FIG. 13 is a perspective view of the clamping apparatus of the inspection station of FIG. 9.

As illustrated in FIGS. 14 and 15, tubular members 89 inspected on inspection station 11' are not perfectly cylindrical but may include a bend or bow. When supported between first pole 95 and second pole 99, the poles 95, 99 exert a magnetic force on end 91, pulling end 91 of tubular member 89 toward first pole 95 or second pole 99. When tubular member 89 is perfectly cylindrical, the magnetic forces will balance out and end 91 of tubular member 89 will maintain its position between first pole 95 and second pole 99. When tubular member 89 bows or bends, end 91 can be closer to one of first pole 95 and second pole 99, thus, when the magnetic fields are passed through end 91 while end 91 is rotated, end 91 will be pulled into contact with first pole 95 or second pole 99. To compensate for this, first compensating piston 107 and second compensating piston 109 provide reactive forces in response to the pulling of end 91 toward one of first pole 95 or second pole 99 to prevent end 91 from contacting first pole 95 or second pole 99, thereby maintaining end 91 between first and second poles 95, 99 for inspection of end 91. In an example embodiment, first and second compensating pistons 107, 109 may be actuable pistons controlled by a programmable logic controller adapted to actuate the first and second compensating pistons 107, 109 when an increase in force is detected at the first and second rollers 117, 125. In another example embodiment, First and second compensating pistons 107, 109, may be fluid cylinders relying on fluid friction within each cylinder to resist a compressive force exerted on first and second roller 117, 125 by tubular member 89 when tubular member 89 subject to the magnetic forces of LFDA 79. In still another example embodiment, first and second rollers 117, 125 and first and second compensating pistons 107, 109 include positions sensors that detect a change in physical position during the testing process. In response to a predetermined amount of physical position change, first and second compensating pistons 107, 109 may actuate, for example, where first and second compensating pistons 107, 109 are hydraulic or pneumatic pistons, hydraulic fluid pressure or pneumatic pressure may be applied to the first and second compensating pistons 107, 109 to ensure that first and second roller 117, 125 and thus, tubular member 89 maintain the desire position. In still another example, first and second compensating pistons 107, 109 may be air springs having parallel plumbing controlled through a variable pressure regulator to provide resistive forces against tubular member 89.

As shown in FIG. 16, inspection station 11' may be positioned adjacent two a second inspection station 11', each having a separate clamping apparatus 103. When installed in this manner, two pipe ends or two pipe couplers may be inspected simultaneously, increasing the efficiency of the inspection process and reducing total costs of inspection.

The disclosed embodiments provide several advantages over the prior art. For example, the disclosed embodiments provide a magnetic inspection assembly that may inspect the ends of a tubular member or a short tubular coupler. In addition, the disclosed embodiments provide an inspection apparatus that does not leave the tubular member or coupler magnetized following the inspection process. Still further, the disclosed embodiments provide an apparatus that prevents contact between the tubular member and the inspection apparatus during the inspection process, thereby limiting damage to the ends are and the inspection apparatus.

This application claims priority to and the benefit of copending U.S. Provisional Application No. 61/460,785, filed on Jan. 7, 2011, entitled "Method and Apparatus for Special End Area Inspection" to Carroll Roy Thompson which application is hereby incorporated in its entirety herein by reference.

While the invention has been shown or described in only some of its forms, it should be apparent to those skilled in the art that it is not so limited, but is susceptible to various changes without departing from the scope of the invention.

What is claimed is:

1. A magnetic inspection system to inspect test tubular member ends and couplers, the magnetic inspection system comprising:
   a longitudinal flaw detection assembly (LFDA) that generates a magnetic field that passes circumferentially through the end of the tubular member;
   a transverse flaw detection assembly (TFDA) that generates a magnetic field that passes longitudinally through the end of the tubular member;
   an inspection station frame assembly positioned on a substantially planar horizontal surface, the LFDA and the TFDA mounted to the inspection station frame assembly so that the LFDA and the TFDA are spaced-apart from the substantially planar horizontal surface, the LFDA and the TFDA positioned on the inspection station frame assembly so that the end of the tubular member is positioned in both the LFDA and the TFDA;
   a magnetic particle inspection (MPI) insertion apparatus adapted to coat the tubular member in an MPI fluid, the MPI fluid having a plurality of ferromagnetic particles suspended therein, the ferromagnetic particles appearing fluorescent when exposed to an ultraviolet light;
   an ultraviolet light assembly adapted to expose an exterior surface of the tubular member to ultraviolet light and an interior surface of the tubular member to ultraviolet light; and
   a tubular member clamping apparatus positioned closely adjacent to and separate from the inspection station frame assembly, the tubular member clamping apparatus adapted to support the tubular member within the LFDA and the TFDA, rotate the tubular member within the LFDA and the TFDA about an axis of the tubular member that is substantially parallel to the substantially planar horizontal surface, the tubular member clamping apparatus exerts a compensating force on the tubular member that resists the magnetic forces of the LFDA exerted on the tubular member during inspection of the tubular member.

2. The magnetic inspection system of claim 1, wherein the tubular member clamping apparatus comprises:
   a vertical support beam mounted to the substantially horizontal surface;
   a first and second compensating piston assembly each having lower ends mounted to opposite sides of the vertical support beam;
   pivotable rollers mounted on ends of the respective compensating piston assemblies opposite the vertical support beam, the pivotable rollers supporting the tubular member;
   a clamping piston assembly coupled to a motorized roller to clamp the tubular member between the pivotable rollers and the clamping piston while rotating the tubular member; and
   wherein when the LFDA exerts a magnetic force on the tubular member pulling the tubular member toward a pole of the LFDA, the compensating pistons exert reactive forces on the tubular member to push one or more of the pivotable rollers into tighter contact with the tubular member.

3. The magnetic inspection system of claim 2, wherein the vertical support beam has an adjustable height.

4. The magnetic inspection system of claim 2, further comprising a stop limiter knob mounted to the vertical support beam so that the stop limiter knob limits the total amount of pivoting by the pivotable rollers.

5. The magnetic inspection system of claim 1, wherein the LFDA comprises:
   a yoke having coils, side circuit elements, upper circuit elements, and a base circuit element, lower ends of the side elements perpendicularly join the base element at opposing ends of the base element, the upper ends of the side elements perpendicularly join ends of the upper circuit elements to position the upper circuit elements over the base circuit element and form a gap between free ends of the upper circuit elements, the gap has a width slightly larger than an outer diameter of the tubular member so that the tubular member is proximate to the free ends of the upper circuit elements when the tubular member is positioned for inspection;
   the coils include wire wound around the side circuit elements and coupled to a DC power supply so that coils receive an electric current to induce a magnetic field in the side, upper, and base circuit elements that passes circumferentially through a wall of the tubular member when the tubular member is positioned for inspection; and
   rails mounted to the inspection station frame assembly, the yoke mounted to the rails so that the yoke may move relative to the tubular member parallel to the axis of the tubular member.

6. The magnetic inspection system of claim 1, wherein the LFDA comprises:
   a first magnetic coil magnetically coupled to a first magnetic pole;
   a second magnetic coil magnetically coupled to a second magnetic pole;
   wherein the first and second magnetic poles are adapted to form a magnetic circuit across a gap formed between the first magnetic pole and the second magnetic pole, when the tubular member is positioned for inspection, the tubular member will be positioned between the first magnetic pole and the second magnetic pole;
   wherein power is supplied to the first magnetic coil and the second magnetic coil to magnetically polarize the respective magnetic poles with opposite magnetic polarization to generate a magnetic field across the gap and the tubular member; and
   wherein the first magnetic pole and the second magnetic pole have a length substantially equivalent to a length of a portion of the tubular member to be inspected, allowing inspection of the entirety of the desired portion of the tubular member.

7. The magnetic inspection system of claim 1, wherein the TFDA comprises:
   an electromagnetic ring positioned to be coaxial with the axis of the tubular member when the tubular member is positioned for inspection, the electromagnetic ring having a wire coil wound coaxial with the electromagnetic ring within a housing, the wire coil coupled to a DC power supply to supply a current to the wire coil to induce a magnetic field that passes longitudinally through the tubular member when the tubular member is positioned for inspection; and rails mounted to the inspection station frame assembly, the housing mounted to the rails so that the housing may move parallel to the axis of the tubular member when the tubular member is positioned for inspection.

8. The magnetic inspection system of claim 1, wherein the TFDA comprises:

a first electromagnetic ring mounted to the inspection station frame assembly;

a second electromagnetic ring mounted to the inspection station frame assembly coaxial with first electromagnetic ring, both the first and second electromagnetic rings coaxial with the axis of the tubular member when the tubular member is positioned for inspection; and wherein the first and second electromagnetic rings each include a wire coil wound coaxial with the axis of the tubular member when the tubular member is positioned for inspection, the wire coil of each electromagnetic ring coupled to a DC power supply to supply a current to the wire coil to induce a magnetic field adapted to pass longitudinally through the tubular member.

9. The magnetic system of claim 1, further comprising a second magnetic inspection station having a longitudinal flaw detection assembly (LFDA), a transverse flaw detection assembly (TFDA), an inspection station frame assembly, a magnetic particle inspection (MPI) insertion apparatus, an ultraviolet light assembly, and a tubular member clamping apparatus, the second magnetic inspection station positioned to inspect portions of two tubular members at substantially the same time.

10. A magnetic inspection system to inspect tubular member ends and tubular couplers, the magnetic inspection system comprising:

a longitudinal flaw detection assembly (LFDA) that generates a magnetic field that passes circumferentially through the end of the tubular member;

a transverse flaw detection assembly (TFDA) that generates a magnetic field that passes longitudinally through the end of the tubular member;

an inspection station frame assembly positioned on a substantially planar horizontal surface, the LFDA and the TFDA mounted to the inspection station frame assembly so that the LFDA and the TFDA are spaced-apart from the substantially planar horizontal surface, the LFDA and the TFDA positioned on the inspection station frame assembly so that the end of the tubular member is positioned in both the LFDA and the TFDA;

a magnetic particle inspection (MPI) insertion apparatus adapted to coat the tubular member in an MPI fluid, the MPI fluid having a plurality of ferromagnetic particles suspended therein, the ferromagnetic particles appearing fluorescent when exposed to an ultraviolet light;

an ultraviolet light assembly adapted to expose an exterior surface of the tubular member to ultraviolet light and an interior surface of the tubular member to ultraviolet light;

a tubular member clamping apparatus positioned closely adjacent to and separate from the inspection station frame assembly, the tubular member clamping apparatus adapted to support the tubular member within the LFDA and the TFDA, rotate the tubular member within the LFDA and the TFDA about an axis of the tubular member that is substantially parallel to the substantially planar horizontal surface, the tubular member clamping apparatus exerts a compensating force on the tubular member that resists the magnetic forces of the LFDA exerted on the tubular member during inspection of the tubular member; and the tubular member clamping apparatus including:

a vertical support beam mounted to the substantially horizontal surface;

a first and second compensating piston assembly each having lower ends mounted to opposite sides of the vertical support beam;

pivotable rollers mounted on ends of the respective compensating piston assemblies opposite the vertical support beam, the pivotable rollers supporting the tubular member;

a clamping piston assembly coupled to a motorized roller to clamp the tubular member between the pivotable rollers and the clamping piston while rotating the tubular member; and wherein when the LFDA exerts a magnetic force on the tubular member pulling the tubular member toward a pole of the LFDA, the compensating pistons exert reactive forces on the tubular member to push one or more of the pivotable rollers into tighter contact with the tubular member.

11. The magnetic inspection system of claim 10, wherein the vertical support beam has an adjustable height.

12. The magnetic inspection system of claim 10, further comprising a stop limiter knob mounted to the vertical support beam so that the stop limiter knob limits the total amount of pivoting by the pivotable rollers.

13. The magnetic inspection system of claim 10, wherein the LFDA comprises:

a yoke having coils, side circuit elements, upper circuit elements, and a base circuit element, lower ends of the side elements perpendicularly join the base element at opposing ends of the base element, the upper ends of the side elements perpendicularly join ends of the upper circuit elements to position the upper circuit elements over the base circuit element and form a gap between free ends of the upper circuit elements, the gap has a width slightly larger than an outer diameter of the tubular member so that the tubular member is proximate to the free ends of the upper circuit elements when the tubular member is positioned for inspection;

the coils include wire wound around the side circuit elements and coupled to a DC power supply so that coils receive an electric current to induce a magnetic field in the side, upper, and base circuit elements that passes circumferentially through a wall of the tubular member when the tubular member is positioned for inspection; and rails mounted to the inspection station frame assembly, the yoke mounted to the rails so that the yoke may move relative to the tubular member parallel to the axis of the tubular member.

14. The magnetic inspection system of claim 10, wherein the LFDA comprises:

a first magnetic coil magnetically coupled to a first magnetic pole;

a second magnetic coil magnetically coupled to a second magnetic pole;

wherein the first and second magnetic poles are adapted to form a magnetic circuit across a gap formed between the first magnetic pole and the second magnetic pole, when the tubular member is positioned for inspection, the tubular member will be positioned between the first magnetic pole and the second magnetic pole;

wherein power is supplied to the first magnetic coil and the second magnetic coil to magnetically polarize the respective magnetic poles with opposite magnetic polarization to generate a magnetic field across the gap and the tubular member; and wherein the first magnetic pole and the second magnetic pole have a length substantially equivalent to a length of a portion of the tubular member to be inspected, allowing inspection of the entirety of the desired portion of the tubular member.

15. The magnetic inspection system of claim 10, wherein the TFDA comprises:
an electromagnetic ring positioned to be coaxial with the axis of the tubular member when the tubular member is positioned for inspection, the electromagnetic ring having a wire coil wound coaxial with the electromagnetic ring within a housing, the wire coil coupled to a DC power supply to supply a current to the wire coil to induce a magnetic field that passes longitudinally through the tubular member when the tubular member is positioned for inspection; and
rails mounted to the inspection station frame assembly, the housing mounted to the rails so that the housing may move parallel to the axis of the tubular member when the tubular member is positioned for inspection.

16. The magnetic inspection system of claim 10, wherein the TFDA comprises:
a first electromagnetic ring mounted to the inspection station frame assembly;
a second electromagnetic ring mounted to the inspection station frame assembly coaxial with first electromagnetic ring, both the first and second electromagnetic rings coaxial with the axis of the tubular member when the tubular member is positioned for inspection; and
wherein the first and second electromagnetic rings each include a wire coil wound coaxial with the axis of the tubular member when the tubular member is positioned for inspection, the wire coil of each electromagnetic ring coupled to a DC power supply to supply a current to the wire coil to induce a magnetic field adapted to pass longitudinally through the tubular member.

17. A method for inspecting tubular members comprising:
(a) inserting a tubular member into a longitudinal flaw detection apparatus (LFDA) and a transverse flaw detection apparatus (TFDA), the tubular member supported by a clamping apparatus adapted to rotate the tubular member on an axis of the tubular member;
(b) rotating the tubular member with a motorized roller of the clamping apparatus;
(c) passing a magnetic field generated by the LFDA circumferentially through the tubular member while spraying the interior and exterior of the tubular member with a magnetic particle inspection (MPI) fluid having a plurality of ferromagnetic particles that appear fluorescent when exposed to ultraviolet light;
(d) exposing the interior and exterior of the tubular member to ultraviolet light and identifying areas of congregated MPI in response to the circumferential passage of the magnetic field;
(e) passing a magnetic field generated by the TFDA longitudinally through the tubular member while spraying the interior and exterior of the tubular member with the MPI fluid;
(f) exposing the interior and exterior of the tubular member to ultraviolet light and identifying areas of congregated MPI in response to the longitudinal passage of the magnetic field; and
(g) in response to generation of magnetic forces by the magnetic fields, exerting a counteracting force on the tubular member with the clamping apparatus, preventing contact between the tubular member and the LFDA and the TFDA.

18. The method of claim 17, further comprising:
performing step (c) prior to performing step (e); and
removing the LFDA magnetic field from the tubular member prior to performing step (e).

19. The method of claim 17, wherein step (g) further comprises applying a counteracting force with one or more compensating pistons coupled to the clamping apparatus and adapted to support the weight of the tubular member when the clamping apparatus supports the tubular member.

20. The method of claim 17, wherein the method further comprises:
passing a magnetic field generated by the LFDA circumferentially through the tubular member with an opposite polarity from the field generated to inspect the tubular member;
passing a magnetic field generated by the TFDA longitudinally through the tubular member with an opposite polarity from the field generated to inspect the tubular member; and
wherein the passage of the oppositely polarized magnetic fields through the tubular member removes residual magnetism of the tubular member.

* * * * *